(12) United States Patent
Bouchard et al.

(10) Patent No.: US 9,170,212 B2
(45) Date of Patent: *Oct. 27, 2015

(54) METHOD AND SYSTEM FOR PERFORMING INSPECTION OF A LIQUID PRODUCT AT A SECURITY CHECKPOINT

(71) Applicant: OPTOSECURITY INC., Québec (CA)

(72) Inventors: Michel Bouchard, Saint-Augustin-de-Desmaures (CA); Dan Gudmundson, Québec (CA); Eric Bourbeau, Québec (CA)

(73) Assignee: OPTOSECURITY INC., Quebec, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/244,213

(22) Filed: Apr. 3, 2014

(65) Prior Publication Data

US 2014/0211980 A1 Jul. 31, 2014

Related U.S. Application Data

(63) Continuation of application No. 12/680,625, filed as application No. PCT/CA2009/000395 on Mar. 27, 2009, now Pat. No. 8,867,816.

(60) Provisional application No. 61/094,743, filed on Sep. 5, 2008, provisional application No. 61/097,060, filed on Sep. 15, 2008, provisional application No. 61/151,242, filed on Feb. 10, 2009.

(30) Foreign Application Priority Data

Nov. 17, 2008 (WO) ................ PCT/CA2008/002025

(51) Int. Cl.
*G01N 23/00* (2006.01)
*G01N 9/24* (2006.01)
(Continued)

(52) U.S. Cl.
CPC .............. *G01N 23/00* (2013.01); *G01F 23/288* (2013.01); *G01N 9/24* (2013.01); *G01N 23/04* (2013.01);
(Continued)

(58) Field of Classification Search
CPC ....... G01N 23/00; G01N 23/02; G01N 23/04; G01N 23/046; G01N 23/10; G01N 23/087; G01N 2223/637; G01N 2001/024; G01N 9/24; G01B 11/22; G01B 11/26; G01B 11/24; G01B 15/06; G01B 15/04; G01F 1/662; G01F 1/667; G01F 23/288; G01F 25/0061; G01F 25/0069; G03F 7/70341; G03F 7/707; G03F 7/20; G03F 7/70516

See application file for complete search history.

(56) References Cited

U.S. PATENT DOCUMENTS

| 3,342,397 | A | 9/1967 | Duitsman |
| 3,589,511 | A | 6/1971 | Britt |

(Continued)

FOREIGN PATENT DOCUMENTS

| CA | 2574402 A1 | 1/2006 |
| CA | 2623812 A1 | 5/2007 |

(Continued)

OTHER PUBLICATIONS

International Search Report and Written Opinion both mailed Jan. 10, 2008 in connection with International Patent Application PCT/CA2007/001658.

(Continued)

*Primary Examiner* — Manav Seth
(74) *Attorney, Agent, or Firm* — Ladas & Parry LLP

(57) ABSTRACT

A method, an apparatus and a system are provided for assessing at a security checkpoint the threat status of a liquid product comprised of a bottle at least partially filled with liquid. Generally, an X-ray image of the liquid product is obtained and processed to derive a level of fill of the bottle and the threat status of the liquid product is determined at least in part based on the level of fill of the bottle. In some examples presented, an X-ray image of the liquid product is processed to derive location information associated with a meniscus formed by the liquid in the bottle and an estimated length of a path followed by X-rays through the liquid held in the bottle is used to determine the threat status of the liquid product, the length of the path being derived in part based on the location information.

29 Claims, 20 Drawing Sheets

(51) Int. Cl.
 G01F 23/288 (2006.01)
 G01N 23/04 (2006.01)
 G06K 9/00 (2006.01)
 G06K 9/62 (2006.01)
 G06T 7/00 (2006.01)
 G01N 1/02 (2006.01)

(52) U.S. Cl.
 CPC ......... *G06K 9/00771* (2013.01); *G06K 9/6267* (2013.01); *G06T 7/00* (2013.01); *G01N 2001/024* (2013.01); *G01N 2223/637* (2013.01); *G01N 2223/639* (2013.01)

(56) References Cited

U.S. PATENT DOCUMENTS

| | | |
|---|---|---|
| 3,609,045 A | 9/1971 | Stein |
| 3,673,394 A | 6/1972 | Hartmann |
| 4,075,700 A | 2/1978 | Blay |
| 4,392,237 A | 7/1983 | Houston |
| 4,454,949 A | 6/1984 | Flum |
| 4,497,065 A | 1/1985 | Tisdale et al. |
| 4,709,333 A | 11/1987 | Crawford |
| 4,727,562 A | 2/1988 | Belanger |
| 4,864,142 A | 9/1989 | Gomberg |
| 4,870,666 A | 9/1989 | Lonn |
| 4,927,022 A | 5/1990 | Wilson |
| 4,962,515 A | 10/1990 | Kopans |
| 4,974,247 A | 11/1990 | Friddell |
| 4,985,906 A | 1/1991 | Arnold |
| 5,027,378 A | 6/1991 | Fujii et al. |
| 5,044,002 A | 8/1991 | Stein |
| 5,056,124 A | 10/1991 | Kakimoto et al. |
| 5,400,381 A | 3/1995 | Steude et al. |
| 5,428,657 A | 6/1995 | Papanicolopoulos et al. |
| 5,442,672 A | 8/1995 | Bjorkholm et al. |
| 5,490,218 A | 2/1996 | Krug et al. |
| 5,524,133 A | 6/1996 | Neale et al. |
| 5,557,108 A | 9/1996 | Tumer |
| 5,568,262 A | 10/1996 | LaChapelle et al. |
| 5,600,303 A | 2/1997 | Husseiny et al. |
| 5,600,700 A | 2/1997 | Krug et al. |
| 5,602,890 A | 2/1997 | Gray et al. |
| 5,692,029 A | 11/1997 | Husseiny et al. |
| 5,768,334 A | 6/1998 | Maitrejean et al. |
| 5,838,758 A | 11/1998 | Krug et al. |
| 5,864,600 A | 1/1999 | Gray et al. |
| 5,974,111 A | 10/1999 | Krug et al. |
| 6,018,562 A | 1/2000 | Willson |
| 6,026,171 A | 2/2000 | Hiraoglu et al. |
| 6,041,132 A | 3/2000 | Isaacs et al. |
| 6,054,712 A | 4/2000 | Komardin et al. |
| 6,069,936 A | 5/2000 | Bjorkholm |
| 6,078,642 A | 6/2000 | Simanovsky et al. |
| 6,088,423 A | 7/2000 | Krug et al. |
| 6,122,344 A | 9/2000 | Beevor |
| 6,175,655 B1 | 1/2001 | George et al. |
| 6,201,850 B1 | 3/2001 | Heumann |
| 6,542,574 B2 | 4/2003 | Grodzins |
| 6,654,445 B2 | 11/2003 | Shepherd et al. |
| 6,707,381 B1 | 3/2004 | Maloney |
| 6,707,879 B2 | 3/2004 | McClelland et al. |
| 6,721,387 B1 | 4/2004 | Naidu et al. |
| 6,721,391 B2 | 4/2004 | McClelland et al. |
| 6,753,527 B1 | 6/2004 | Yamagishi et al. |
| 6,763,083 B2 | 7/2004 | Fernandez |
| H002110 H | 10/2004 | Newman |
| 6,840,120 B2 | 1/2005 | Sakairi et al. |
| 6,952,163 B2 | 10/2005 | Huey et al. |
| 7,033,070 B2 | 4/2006 | Azami |
| 7,065,175 B2 | 6/2006 | Green |
| 7,092,485 B2 | 8/2006 | Kravis |
| 7,149,339 B2 | 12/2006 | Veneruso |
| 7,154,985 B2 | 12/2006 | Dobbs et al. |
| 7,164,750 B2 | 1/2007 | Nabors et al. |
| 7,257,188 B2 | 8/2007 | Bjorkholm |
| 7,260,254 B2 | 8/2007 | Highnam et al. |
| 7,274,768 B2 | 9/2007 | Green |
| 7,317,390 B2 | 1/2008 | Huey et al. |
| 7,355,402 B1 | 4/2008 | Taicher et al. |
| 7,386,093 B2 | 6/2008 | Wu et al. |
| 7,508,908 B2 | 3/2009 | Hu et al. |
| 7,614,788 B2 | 11/2009 | Gatten |
| 7,684,605 B2 | 3/2010 | Klingenbeck-Regn |
| 7,727,567 B2 * | 6/2010 | Heuft ............................ 426/232 |
| 7,787,681 B2 | 8/2010 | Zhang et al. |
| 7,789,401 B2 | 9/2010 | Ambrefe, Jr. |
| 7,840,360 B1 | 11/2010 | Micheels et al. |
| 7,869,637 B2 | 1/2011 | Baumgart et al. |
| 7,873,201 B2 | 1/2011 | Eilbert et al. |
| 7,945,017 B2 | 5/2011 | Chen et al. |
| 8,090,150 B2 | 1/2012 | Garms |
| 8,116,428 B2 | 2/2012 | Gudmundson et al. |
| 8,150,105 B2 | 4/2012 | Mian et al. |
| 8,260,020 B2 | 9/2012 | Garms |
| 8,831,331 B2 | 9/2014 | Gudmundson et al. |
| 8,867,816 B2 | 10/2014 | Bouchard et al. |
| 8,879,791 B2 | 11/2014 | Drouin et al. |
| 2001/0033636 A1 | 10/2001 | Hartick et al. |
| 2002/0097833 A1 | 7/2002 | Kaiser et al. |
| 2003/0062373 A1 | 4/2003 | Holland |
| 2004/0016271 A1 | 1/2004 | Shah et al. |
| 2004/0101097 A1 | 5/2004 | Wakayama et al. |
| 2004/0232092 A1 | 11/2004 | Cash |
| 2004/0252024 A1 | 12/2004 | Huey et al. |
| 2005/0036689 A1 | 2/2005 | Mahdavieh |
| 2005/0058242 A1 | 3/2005 | Peschmann |
| 2005/0078801 A1 | 4/2005 | Georgeson et al. |
| 2005/0111618 A1 | 5/2005 | Sommer, Jr. et al. |
| 2005/0117700 A1 | 6/2005 | Peschmann |
| 2005/0173284 A1 | 8/2005 | Ambrefe, Jr. |
| 2005/0193648 A1 | 9/2005 | Klein et al. |
| 2005/0226360 A1 | 10/2005 | Kaucic et al. |
| 2005/0238232 A1 | 10/2005 | Ying et al. |
| 2006/0013464 A1 | 1/2006 | Ramsay et al. |
| 2006/0022140 A1 | 2/2006 | Connely et al. |
| 2006/0054682 A1 | 3/2006 | de la Huerga |
| 2006/0078085 A1 | 4/2006 | Zanker |
| 2006/0086794 A1 | 4/2006 | Knowles et al. |
| 2006/0098773 A1 | 5/2006 | Peschmann |
| 2006/0115044 A1 | 6/2006 | Wu et al. |
| 2006/0133566 A1 | 6/2006 | Li et al. |
| 2006/0187221 A1 | 8/2006 | Lakare et al. |
| 2006/0193434 A1 | 8/2006 | Green |
| 2006/0203960 A1 | 9/2006 | Schlomka et al. |
| 2006/0239402 A1 | 10/2006 | Hu et al. |
| 2006/0257005 A1 | 11/2006 | Bergeron et al. |
| 2007/0003009 A1 | 1/2007 | Gray |
| 2007/0013519 A1 | 1/2007 | Chung et al. |
| 2007/0041612 A1 | 2/2007 | Perron et al. |
| 2007/0041613 A1 | 2/2007 | Perron et al. |
| 2007/0058037 A1 | 3/2007 | Bergeron et al. |
| 2007/0098142 A1 | 5/2007 | Rothschild et al. |
| 2007/0132580 A1 | 6/2007 | Ambrefe, Jr. |
| 2007/0133743 A1 | 6/2007 | Johnson et al. |
| 2007/0152033 A1 | 7/2007 | Hind et al. |
| 2007/0168467 A1 | 7/2007 | Hu et al. |
| 2007/0192850 A1 | 8/2007 | Cowburn |
| 2007/0217571 A1 | 9/2007 | Teslyar et al. |
| 2007/0297560 A1 | 12/2007 | Song et al. |
| 2008/0056443 A1 | 3/2008 | Hu et al. |
| 2008/0062262 A1 | 3/2008 | Perron et al. |
| 2008/0063140 A1 | 3/2008 | Awad |
| 2008/0116267 A1 | 5/2008 | Barber |
| 2008/0138475 A1 | 6/2008 | Heuft |
| 2008/0152082 A1 | 6/2008 | Bouchard et al. |
| 2008/0167552 A1 | 7/2008 | Bouchevreau et al. |
| 2008/0170660 A1 | 7/2008 | Gudmundson et al. |
| 2008/0181473 A1 | 7/2008 | Garty et al. |
| 2008/0240578 A1 | 10/2008 | Gudmundson et al. |
| 2008/0253627 A1 | 10/2008 | Boyden et al. |
| 2008/0283761 A1 | 11/2008 | Robinson et al. |
| 2008/0312768 A1 | 12/2008 | Ewing et al. |
| 2009/0003514 A1 | 1/2009 | Edic et al. |

(56) References Cited

U.S. PATENT DOCUMENTS

| | | | |
|---|---|---|---|
| 2009/0060135 | A1 | 3/2009 | Morton |
| 2009/0123051 | A1 | 5/2009 | Tamai et al. |
| 2009/0146061 | A1 | 6/2009 | Manneschi |
| 2009/0168963 | A1 | 7/2009 | Harding |
| 2009/0175411 | A1 | 7/2009 | Gudmundson et al. |
| 2009/0180591 | A1 | 7/2009 | Baumgart |
| 2009/0196396 | A1 | 8/2009 | Doyle et al. |
| 2009/0252295 | A1 | 10/2009 | Foland |
| 2010/0027741 | A1 | 2/2010 | Doyle et al. |
| 2010/0046704 | A1 | 2/2010 | Song et al. |
| 2010/0074483 | A1 | 3/2010 | Janes |
| 2010/0127169 | A1 | 5/2010 | Whittum et al. |
| 2010/0208972 | A1* | 8/2010 | Bouchard et al. ............. 382/132 |
| 2010/0220910 | A1 | 9/2010 | Kaucic et al. |
| 2010/0277312 | A1 | 11/2010 | Edic et al. |
| 2010/0284514 | A1 | 11/2010 | Zhang et al. |
| 2010/0329532 | A1 | 12/2010 | Masuda et al. |
| 2011/0007870 | A1 | 1/2011 | Roux et al. |
| 2011/0172972 | A1 | 7/2011 | Gudmundson et al. |
| 2011/0243299 | A1 | 10/2011 | Sugita et al. |
| 2012/0093367 | A1 | 4/2012 | Gudmundson et al. |
| 2012/0275646 | A1 | 11/2012 | Drouin et al. |
| 2014/0198699 | A1 | 7/2014 | Ziskin et al. |
| 2014/0241495 | A1 | 8/2014 | Gudmundson et al. |
| 2014/0321729 | A1 | 10/2014 | Gudmundson et al. |
| 2015/0010128 | A1 | 1/2015 | Drouin et al. |

FOREIGN PATENT DOCUMENTS

| | | |
|---|---|---|
| CA | 2666838 C | 3/2008 |
| CA | 2676913 C | 11/2010 |
| CA | 2700553 C | 4/2011 |
| CA | 2709468 C | 6/2011 |
| CA | 2690163 C | 8/2011 |
| CA | 2651728 C | 4/2012 |
| CA | 2692662 C | 6/2012 |
| CA | 2696031 C | 8/2012 |
| EP | 2189785 A1 | 5/2010 |
| EP | 2696196 | 2/2014 |
| EP | 2331944 | 3/2014 |
| EP | 2334565 | 3/2014 |
| GB | 2420683 A | 5/2006 |
| GB | 2441551 A | 3/2008 |
| JP | 2006-214725 A | 8/2006 |
| WO | 94/12855 A1 | 6/1994 |
| WO | 98/02763 A1 | 1/1998 |
| WO | 99/45371 A1 | 9/1999 |
| WO | 03/052398 A1 | 6/2003 |
| WO | WO 2004/054329 | 6/2004 |
| WO | 2006/119603 A1 | 11/2006 |
| WO | 2008/009134 A1 | 1/2008 |
| WO | 2008/019473 A1 | 2/2008 |
| WO | 2008/034232 A1 | 3/2008 |
| WO | 2008/036456 A1 | 3/2008 |
| WO | 2008/040119 A1 | 4/2008 |
| WO | 2008/119151 A1 | 10/2008 |
| WO | 2009/024618 A1 | 2/2009 |
| WO | 2009/043145 A1 | 4/2009 |
| WO | 2009/046529 A1 | 4/2009 |
| WO | 2009/114928 A1 | 9/2009 |
| WO | 2009/127353 A1 | 10/2009 |
| WO | 2010/025538 A1 | 3/2010 |
| WO | 2010/025539 A1 | 3/2010 |
| WO | 2010/028474 A1 | 3/2010 |
| WO | 2010/145016 A1 | 12/2010 |

OTHER PUBLICATIONS

Informal Communication with the Applicant issued on Sep. 22, 2008 in connection with International Patent Application PCT/CA2007/001658, 4 pages.

International Preliminary Report on Patentability issued on Dec. 17, 2008 in connection with International Patent Application PCT/CA2007/001658, 7 pages.

International Search Report and Written Opinion both mailed Jan. 14, 2008 in connection with International Patent Application PCT/CA2007/001749, 4 pages.

International Preliminary Report on Patentability issued on Jan. 14, 2008 in connection with International Patent Application PCT/CA2007/001749, 4 pages.

International Search Report and Written Opinion both mailed on Nov. 20, 2008 in connection with International Patent Application PCT/CA2008/001591.

International Preliminary Report on Patentability issued on Sep. 21, 2010 in connection with International Patent Application PCT/CA2008/001591, 7 pages.

International Search Report and Written Opinion both mailed on Dec. 4, 2008 in connection with International Patent Application PCT/CA2008/001721, 5 pages.

International Preliminary Report on Patentability issued on Apr. 15, 2010 in connection with International Patent Application PCT/CA2008/001721, 6 pages.

International Search Report and Written Opinion both mailed on Dec. 5, 2008 in connection with International Patent Application PCT/CA2008/001792.

International Preliminary Report on Patentability issued on Feb. 1, 2010 in connection with International Patent Application PCT/CA2008/001792, 3 pages.

International Preliminary Report and Written Opinion both mailed on Nov. 10, 2009 in connection with International Patent Application PCT/ CA2009/000811.

International Search Report and Written Opinion both mailed on Jun. 4, 2009 in connection with International Patent Application PCT/CA2008/002025.

International Search Report and Written Opinion both mailed on Jul. 6, 2009 in connection with International Patent Application PCT/CA2009/000395.

International Search Report and Written Opinion both mailed on Aug. 6, 2009 in connection with International Patent Application PCT/ CA2009/000401.

International Preliminary Report on Patentability issued on Jan. 12, 2011 in connection with International Patent Application PCT/CA2009/000401, 15 pages.

International Search Report and Written Opinion both mailed on Sep. 22, 2010 in connection with International Patent Application PCT/CA2010/000916.

International Preliminary Report on Patentability issued on Oct. 24, 2011 in connection with International Patent Application PCT/CA2010/000916, 17 pages.

International Search Report and Written Opinion both mailed on Nov. 19, 2010 in connection with International Patent Application PCT/CA2010/001200.

International Preliminary Report on Patentability issued on Nov. 22, 2011 in connection with International Patent Application PCT/CA2010/001200, 12 pages.

Office Action mailed on Jul. 29, 2009 in connection with Canadian Patent Application 2,651,728, 6 pages.

Office Action mailed on Mar. 19, 2010 in connection with Canadian Patent Application 2,651,728 2 pages.

Office Action mailed on Jul. 10, 2009 in connection with Canadian Patent Application 2,666,838, 3 pages.

Benjamin, R., "Object-Based 3D X-Ray Imaging for Second-line Security Screening", European Convention on Security and Detection, 1995. May 16-18, 1995 London, (ABSTRACT ONLY).

Pia Dreiseitel et al. "Detection of liquid explosives using tomosynthetic reconstruction in multiview dual-energy x-ray systems", 1st EU Conference on the Detection of Explosives, held in Avignon, France, from Mar. 14-16, 2011. 4 pages.

Nicolas Freud et al., "Simulation of X-ray NDT Imaging Techniques", Proceedings of the 15th World Conference on Non- Destructive Testing, Rome, Oct. 15-21, 2000, http://www.ndt.net/article/wcndt00/papers/idn256/idn256.htm, pages consulted on Dec. 3, 2009, 7 pages.

Hewei Gao et al., "Application of X-ray CT to liquid security inspection: System analysys and beam hardening correction", Nuclear Instruments & Methods in Physics Research, Section-A:Accelera-

(56) References Cited

OTHER PUBLICATIONS tors, Spectrometers, Detectors and Associated Equipment, Elsevier, Amsterdam, NL, vol. 579, No. 1, pp. 395-399, Available online Apr. 11, 2007.
OPTOSECURITY, "Security Technology Overview: Advanced Vehicle Verification & Threat Identification", 1 page, published prior to Sep. 15, 2008.
D.L. Page et al., "Perception-based 3D Triangle Mesh Segmentation Using Fast Marching Watersheds.", Proc. Intl. Conf. on Computer Vision and Pattern Recognition, vol. II, pp. 27-32, Madison, WI, Jun. 2003.
Guardian Technologies; "PinPoint TM Threat Identification Software", http://guardiantechintl.com/security,php?npage=pinpoint, Jul. 25, 2005, 4 pages.
globalsecurity.org; "Secure Flight Passenger Screening Program", http://globalsecurity.org/security/systems/passenger_screen.htm, Oct. 28, 2005, 6 pages.
M. Sluser et al., "Model-Based Probabilistic Relaxation Segmentation Applied to Threat Detection in Airport X-ray Imagery", Electric and Computer Engineering, 1999 IEEE Canadian Conference on Edmonton, Alta., Canada, May 9 to May 12, 1999 pp. 720-726 vol. 2 XP032158352.
Xiang Li et al., "A numeral simulator in VC++ on PC for iterative image reconstruction", Journal of X-Ray Science and Technology, vol. 11, No. 2, Jan. 1, 2003, pp. 61-70, XP055063644, issn: 0895-3996.
Wei Xie et al., "Simulation of X-ray Imaging Systems for Luggage Inspection", Second Explosives Detection Symposium and Aviation Security Conference, Nov. 12-15, 1996, pp. 248-253.
Notice of Allowance issued on Jan. 16, 2014 in connection with U.S. Appl. No. 13/313,635—10 pages.
Office Action mailed on Nov. 3, 2009 in connection with Canadian Patent Application 2,666,838, 5 pages.
Office Action mailed on Jan. 28, 2010 in connection with Canadian Patent Application 2,666,838, 5 pages.
Office Action mailed on Jan. 28, 2010 in connection with Canadian Patent Application 2,676,913, 2 pages.
Office Action mailed on May 5, 2010 in connection with Canadian Patent Application 2,676,913—2 pages.
Office Action mailed on Mar. 2, 2010 in connection with Canadian Patent Application 2,676,903, 4 pages.
Office Action mailed on Mar. 31, 2010 in connection with Canadian Patent Application 2,690,163—3 pages.
Office Action mailed on May 14, 2010 in connection with Canadian Patent Application 2,690,831—3 pages.
Office Action mailed on Aug. 31, 2010 in connection with Canadian patent application 2,690,831—2 pages.
Office Action mailed on Jun. 7, 2010 in connection with Canadian Patent Application 2,692,662—3 pages.
Office Action mailed on Aug. 31, 2010 in connection with Canadian patent application 2,692,662—3 pages.
Office Action mailed on Jun. 30, 2010 in connection with Canadian patent application 2,696,031—2 pages.
Office Action mailed on Oct. 6, 2010 in connection with Canadian patent application 2,696,031—2 pages.
Office Action mailed on Jun. 28, 2010 in connection with Canadian patent application 2,697,525—3 pages
USPTO NFOA mailed Aug. 5, 2010 in connection with U.S. Appl. No. 12/385,253.
USPTO NFOA mailed Aug. 12, 2010 in connection with U.S. Appl. No. 12/311,522.
USPTO NFOA mailed Sep. 30, 2010 in connection with U.S. Appl. No. 12/311,031.
USPTO NOA mailed Sep. 15, 2011 in connection with U.S. Appl. No. 12/311/031.
Notice of Allowance issued on Feb. 21, 2014 in connection with U.S. Appl. No. 12/864,988—7 pages.
Notice of Allowance issued on Mar. 17, 2014 in connection with U.S. Appl. No. 13/387,578—8 pages.

European Search Report mailed on Apr. 14, 2014 in connection with Europeant Patent Application No. 10788557.6—8 pages.
Examiner's Report mailed on Jul. 9, 2014 in connection with European Patent Application No. 09839849.8—3 pages.
Examiner's Report mailed on Jun. 26, 2014 in connection with European Patent Application No. 07815851.6—4 pages.
Examiner's Report mailed on Jul. 15, 2014 in connection with Canadian Patent Application No. 2,677,439—2 pages.
Notice of Allowance issued on Jun. 25, 2014 in connection with U.S. Appl. No. 13/387,578—8 pages.
Examiner's Report mailed on Aug. 5, 2014 in connection with Canadian Patent Application No. 2,737,075—3 pages.
Office Action mailed on Oct. 29. 2010 in connection with Canadian Patent Application 2.651,728—6 pages.
Office Action mailed on Oct. 28, 2010 in connection with Canadian Patent Application 2,676,903—2 pages.
Office Action mailed on Nov. 2, 2010 in connection with Canadian Patent Application 2,690,163—1 page.
Office Action mailed on Nov. 17, 2010 in connection with Canadian Patent Application 2,709,468—2 pages.
Examiner's Report mailed on Jan. 31, 2011 in connection with Canadian Patent Application 2,697,525—2 pages.
Examiner's Report mailed on Mar. 29, 2011 in connection with Canadian Patent Application 2,725,626—5 pages.
Examiner's Report mailed on Mar. 29, 2011 in connection with Canadian Patent Application 2,690,831—2 pages.
Examiner'S Report mailed on May 2, 2011 in connection with Canadian patent application 2,692,662—3 pages.
Examiner's Report mailed on Jul. 5, 2011 in connection with Canadian patent application 2,596,031—2 pages.
Examiner's Report issued on Jul. 19, 2011 in connection with Canadian patent application 2,651,728—2 pages.
Examiner's Report mailed on Aug. 10, 2011 in connection with Canadian Patent Application 2,725,626—4 pages.
Examiner's Report mailed on Sep. 2, 2011 in connection with Canadian Patent Application 2,737,075—3 pages.
Examiner's Report m iled on Jan. 16, 2013 in connection with Canadian patent application No. 2,697,586—3 Pages.
Examiner's Report mailed on Feb. 4, 2013 in connection with Canadian patent application No. 2,677,439—2 Pages.
Examiner's Report mailed on Jul. 22, 2013 in connection with Canadian Patent Application 2,737,075—3 pages.
Examiner's Report mailed on Jul. 23, 2013 in connection with Canadian Patent Application 2,677,439—2 pages.
Airport Magazine, Solutions, Products, Services, vol. 7, Mar. 2006, 5 pages.
Bottigli et al., "Voxel-based Monte Carlo Simulation of X-Ray imaging and spectroscopy experiments" Spectrochimia Acta. Part B: Atomic Spectroscopy, vol. 59, pp. 1747-1754. XP004598270; Available online Sep. 1, 2004.
EESR dated Jun. 9, 2011 Appln. No. 07815851.6-2204/2064535 PCT/CA2007001658.
EESR dated Nov. 10, 2011 Appln. No. 09810945.7-1240 / 2331944 PCT/CA2009000395.
EESR dated Feb. 1, 2012 Appln. No. 08876865.0-1240 / 2334565 PCT/CA2008002025.
EESR dated Feb. 17, 2012 Appln. No. 08835738.0-2204 /221084 PCT/CA2008001721.
EESR dated Jul. 18, 2012 Appln. No. 09839849.8-1240 / 2396646 PCT/CA2009000811.
EESR dated Dec. 18, 2013 Appln. No. 13191619.9-1559.
EPO Communication dated Jul. 18, 2012; Appln. 09 810 945.7-1240.
EPO Communication dated Aug. 31, 2012 Appln. 07 815 851.6-2204.
EPO Communication dated Nov. 7, 2012 Appln. 08 876 865.0-1240.
EPO Communication dated Apr. 11, 2013 Appln. 08 876 865.0-1559.
EPO Communication dated May 14, 2013 Appln. 09 810 945.7-1559.
EPO Communication dated May 29, 2013 Appln. 09 839 849.8-1559.
USPTO NFOA mailed Mar. 2, 2011 in connection with U.S. Appl. No. 12/311,031.
USPTO NFOA mailed Apr. 20, 2011 in connection with U.S. Appl. No. 12/311,031.

(56) References Cited

OTHER PUBLICATIONS

USPTO NOA mailed Sep. 15, 2011 in connection with U.S. Appl. No. 12/311,031.
USPTO NFOA mailed Feb. 9, 2011 in connection with U.S. Appl. No. 12/311,522.
USPTO NOA mailed May 6, 2011 in connection with U.S. Appl. No. 12/311,522.
USPTO NFOA mailed Feb. 8, 2011 in connection with U.S. Appl. No. 12/385,253.
USPTO NOA mailed May 5, 2011 in connection with U.S. Appl. No. 12/385,253.
USPTO NFOA mailed Feb. 10, 2011 in connection with U.S. Appl. No. 12/680,622.
USPTO NOA mailed May 6, 2011 in connection with U.S. Appl. No. 12/680,622.
USPTO RR dated Mar. 11, 2013 in connection with U.S. Appl. No. 12/680,625.
USPTO NFOA dated Aug. 14, 2013 in connection with U.S. Appl. No. 12/680,625.
USPTO NOA mailed Dec. 2, 2013 in connection with U.S. Appl. No. 12/680.625.
USPTO NFOA dated Mar. 1, 2013 in connection with U.S. Appl. No. 12/681,826.
USPTO RR dated Jun. 14, 2013 in connection with U.S. Appl. No. 12/864,988.
USPTO NFOA dated Oct. 31, 2013 in connection with U.S. Appl. No. 12/864,988.
USPTO NFOA dated Feb. 28, 2013 in connection with U.S. Appl. No. 13/063,869.
USPTO FOA dated Nov. 14, 2013 in connection with U.S. Appl. No. 13/063,869.
USPTO NFOA mailed Sep. 25, 2013 in connection with U.S. Appl. No. 13/313,635.
USPTO NFOA dated Aug. 13, 2014 in connection with U.S. Appl. No. 13/377,872.
Final Office Action issued on Feb. 17, 2015 in connection with U.S. Appl. No. 13/377,872, 23 pages.
Non-Final Office Action issued on Feb. 24, 2015 in connection with U.S. Appl. No. 14/496,676—7 pages.
Examiner's Report issued on Apr. 7, 2015 in connection with Canadian Patent Application No. 2,697,586, 6 pages.
Examiner's Report issued on Jun. 29, 2015 in connection with Canadian Patent Application No. 2,677,439, 3 pages.
Examiner's Report mailed on Jul. 17, 2015 in connection with Canadian Patent Application 2,737,075, 6 pages.
Notice of Allowance issued on Jun. 12, 2015 in connection with U.S. Appl. No. 13/377,872, 8 pages.
Notice of Allowance issued on Jul. 7, 2015 in connection with U.S. Appl. No. 14/496,676, 9 pages.
Non-Final Office Action issued on Jul. 2, 2015 in connection with U.S. Appl. No. 13/063,869, 38 pages.

* cited by examiner

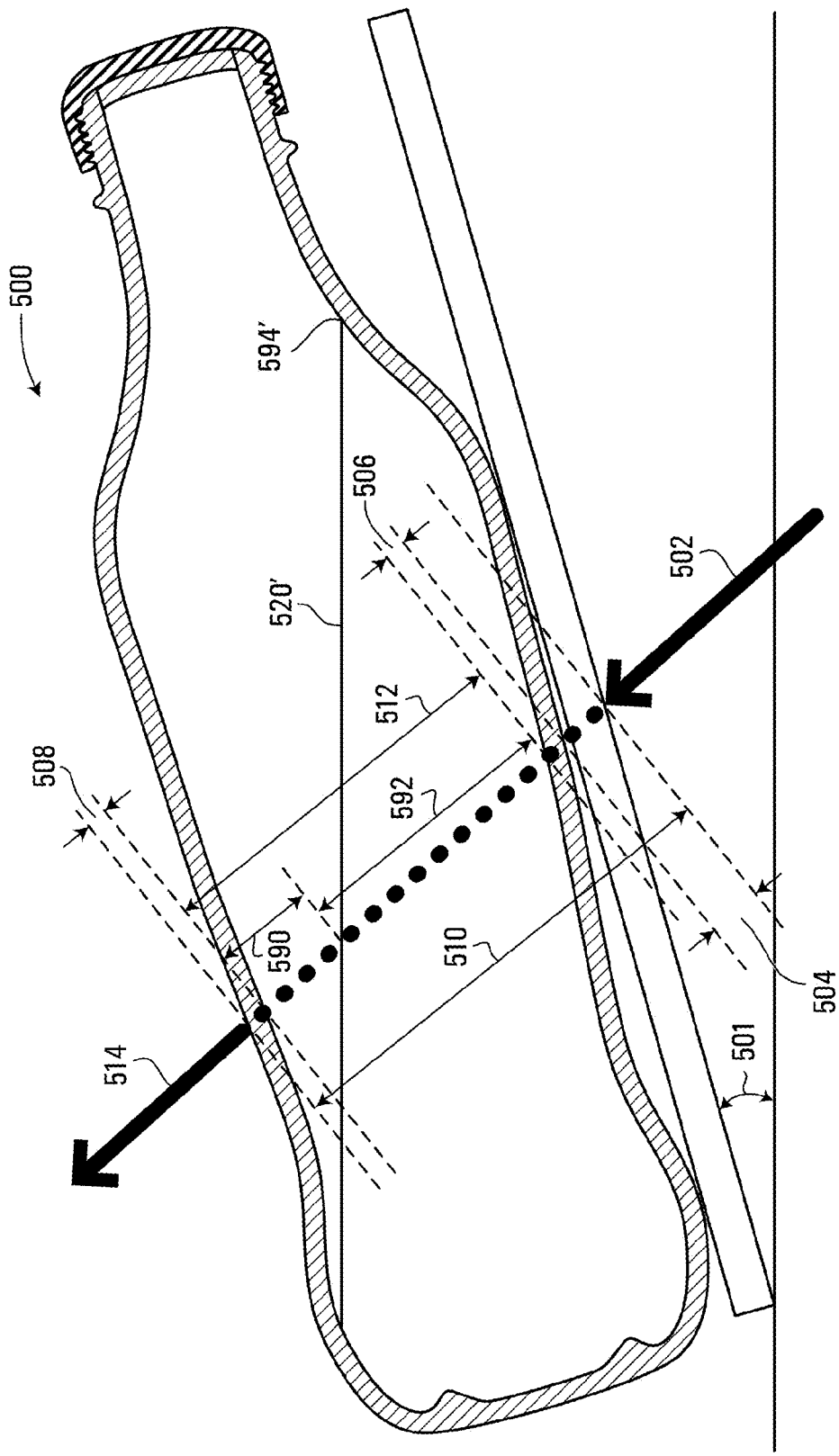

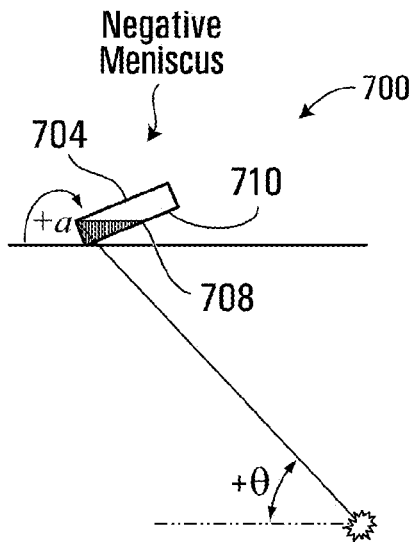
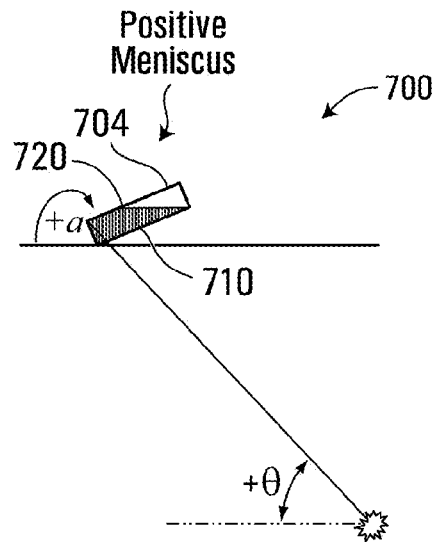
FIG. 7a          FIG. 7b
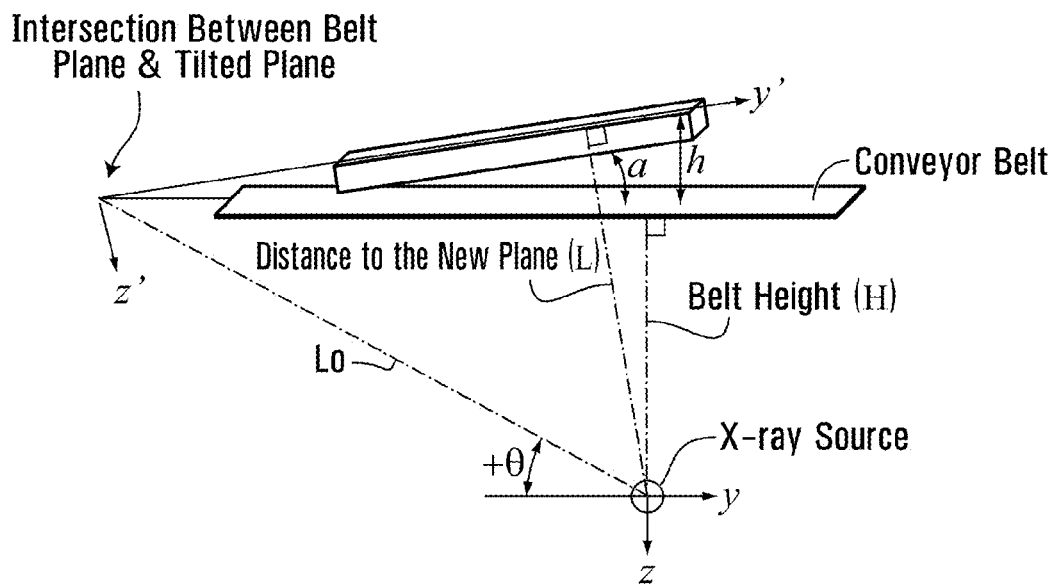
FIG. 8

METHOD AND SYSTEM FOR PERFORMING INSPECTION OF A LIQUID PRODUCT AT A SECURITY CHECKPOINT

CROSS-REFERENCE TO RELATED APPLICATIONS

The present application is a continuation application under 35 USC §120 of U.S. patent application Ser. No. 12/680,625 which was a U.S. national stage entry patent application of international patent application no. PCT/CA2009/000395 filed on Mar. 27, 2009, which in turn, for the purpose of the United States, claimed the benefit of priority:
(1) under 35 USC §120 based on:
 U.S. provisional patent application Ser. No. 61/094,743 filed on Sep. 5, 2008 by Michel Roux et al.;
 U.S. provisional patent application Ser. No. 61/097,060 filed on Sep. 15, 2008 by Michel Roux et al.; and
 U.S. provisional patent application Ser. No. 61/151,242 filed on Feb. 10, 2009 by Luc Perron et al.
and
(2) under 35 USC §119 based on:
 PCT International Patent Application serial number PCT/CA2008/002025 filed in the Canadian Receiving Office on Nov. 17, 2008 by Michel Roux et al. and presently pending.

The present application is also related to:
PCT international Patent Application serial number PCT/CA2008/001721 filed in the Canadian Receiving Office on Sep. 30, 2008 by Michel Roux et al. and presently pending; and
PCT International Patent Application serial number PCT/CA2007/001658 filed in the Canadian Receiving Office on Sep. 17, 2007 by Dan Gudmundson et al.

The contents of the above-referenced patent documents are incorporated herein by reference.

FIELD OF THE INVENTION

The present invention relates to technologies for assessing the threat status of liquid products by means of penetrating radiation such as X-rays. The invention has numerous applications; in particular it can be used for scanning bottles holding liquid substances at airport security check points.

BACKGROUND

Some liquid or combinations of liquid and other compounds may cause enough damage to bring down an aircraft. As no reliable technology-based solution currently exists to adequately address this threat, authorities have implemented a ban of most liquids, gels and aerosols in cabin baggage.

As a result, there have been disruptions in operations (e.g., a longer screening process; a change of focus for screeners; additional line-ups), major inconveniences for passengers (as well as potential health hazards for some) and economic concerns (e.g., increased screening costs; lost revenues for airlines and duty free shops; large quantities of confiscated—including hazardous—merchandise to dispose of), and so on.

In light of the above, there is a need to provide a technology-based solution to assess the threat status of liquid products.

SUMMARY

This patent application focuses on the processing of partially filled bottles of liquid at security check points.

According to a broad aspect, the level of fill of a bottle is used as a factor in the determination of the threat status of the bottle. For example, if the level of fill of the bottle is below a certain threshold level of fill, (e.g. 25% full) then a decision can be made to reject that bottle irrespective of its content. It will be appreciated that deriving the precise level of fill of a bottle, for example 25%, is not critical to the present invention. More specifically, the level of fill may be derived so that it is within a certain tolerance, for example 25% full±10%. Consequently, the level of fill of the bottle can be an approximate measure of the level of fill of the bottle rather than an exact measurement.

In specific examples of implementation, the level of fill of a bottle may be derived based on a visual inspection of the bottle by a security screening and/or based on an x-ray image of the bottle.

According to a specific example of implementation, the level of fill is derived from an x-ray image of the bottle at least in part by extracting from the x-ray image characteristics of the meniscus formed by the liquid held in the bottle. Characteristic of the meniscus may include for example, the shape and position of the meniscus. Any suitable technique for obtaining characteristics pertaining to the meniscus formed by the liquid held in the bottle may be used.

According to another specific example of implementation, the length of a path travelled by X-rays through a liquid held by a bottle is determined from the x-ray image of the bottle, where the bottle is only partially filled with liquid. In accordance with this implementation, location information associated with a meniscus formed by the liquid in the bottle is obtained from the X-ray image. The location information associated with the meniscus is used in combination with geometric information associated with the bottle in the computation of the length of the path travelled by X-rays through the liquid held by the bottle. The determined length of the patent is then used in combination with attenuation information from an x-ray image of the bottle holding the liquid to determine the threat status of the bottle holding the liquid.

In specific implementations, the bottle may be positioned at a known angle (e.g. by means of a tray having an inclined bottom surface), or may be positioned horizontally while it is being scanned by the X-ray machine.

In specific implementations, the X-ray machine used to perform the X-ray inspection may be a single-view machine or a multi-view machine.

In accordance with yet another broad aspect, the present invention provides a method for assessing a threat status of a liquid product at a security checkpoint. The liquid product is comprised of a bottle holding a liquid, wherein the bottle is at least partially filled with liquid. The method comprises receiving X-ray image data associated with the liquid product, the X-ray image data being derived by performing an X-ray scan of the liquid product using an X-ray imaging apparatus. The method also comprises processing the X-ray image data to derive information conveying a level of fill of the bottle and determining the threat status of the liquid product at least in part based on the level of fill of the bottle. The method further comprises releasing information conveying the determined threat status of the liquid product.

In a specific example of implementation, the method comprises processing the X-ray image data to derive information conveying the level of fill of the bottle wherein the processing comprises locating a meniscus formed by the liquid in the bottle.

In a specific example of implementation, the method comprises processing the X-ray image data to derive geometric information associated with the bottle and processing the X-ray image data to derive location information associated with a meniscus formed by the liquid in the bottle. The method also comprises deriving the level of fill of the bottle at least in part based on the location information associated with the meniscus and on the geometric information associated with the bottle.

In a specific example of implementation, the method comprises deriving path length data at least in part based on the location information associated with the meniscus and the geometric information associated with the bottle. The path length data conveys an estimated length of a path followed by X-rays through the liquid held in the bottle. The method also comprises processing the X-ray image data to determine the threat status of the liquid product based in part on the path length data and X-ray attenuation information obtained from the X-ray image data.

In yet another specific example of implementation, the method comprises processing the X-ray image data to derive geometric information associated with the bottle at least in part based on an angle made between a longitudinal axis of the bottle and a horizontal plane and processing the X-ray image data to derive location information associated with a meniscus formed by the liquid in the bottle at least in part based on the angle made between the longitudinal axis of the bottle and the horizontal plane.

In a specific example of implementation, the liquid product is supported by a tray while the liquid product is subjected to an X-ray inspection at a security checkpoint to determine the threat status of the bottle filled with liquid. The bottle has a top extremity and a bottom extremity and the tray is configured to hold the bottle in an inclined position such that a meniscus in the bottle filled with liquid has a tendency to migrate toward one of the extremities of the bottle filled with liquid. Alternatively, the tray may be a conventional tray with a flat bottom surface.

In yet a further specific example of implementation, the method comprises receiving the X-ray image data associated with the liquid product, wherein the X-ray image data is obtained using a multi-view X-ray machine. The X-ray image data conveys a first X-ray image of the liquid product taken by subjecting the liquid product to X-rays in a first orientation and a second X-ray image of the liquid product taken by subjecting the liquid product to X-rays in a second orientation. The method also comprises processing the X-ray image data corresponding to the first X-ray image of the liquid product to derive information conveying an estimated level of fill of the bottle and processing the X-ray image data corresponding to the second X-ray image of the liquid product and the estimated level of fill of the bottle obtained based on the X-ray image data corresponding to the first X-ray image to derive an adjusted level of fill of the bottle. The method further comprises determining the threat status of the liquid product at least in part based on the adjusted level of fill of the bottle and releasing information conveying the determined threat status of liquid product.

In accordance with another broad aspect, the invention provides a computer readable storage medium storing a program element suitable for execution by a computing apparatus for assessing a threat status of a liquid product at a security checkpoint, the liquid product being comprised of a bottle holding a liquid, wherein the bottle is at least partially filled with liquid. The computing apparatus comprises a memory unit and a processor operatively connected to the memory unit. The program element, when executing on the processor, is operative for assessing the threat status of a liquid product in accordance with the above-described method.

In accordance with yet another broad aspect, the invention provides an apparatus for assessing a threat status of a liquid product at a security checkpoint, where the liquid product is comprised of a bottle holding a liquid and wherein the bottle is at least partially filled with liquid. The apparatus comprises an input, a processing unit and an output and is operative for assessing the threat status of a liquid product in accordance with the above-described method.

In accordance with a further broad aspect, the invention provides a system suitable for assessing a threat status of a liquid product at a security checkpoint. The liquid product is comprised of a bottle holding a liquid, wherein the bottle is at least partially filled with liquid. The system comprises an inspection device for performing an X-ray inspection on the liquid product using penetrating radiation to generate an X-ray image of the liquid product. The system also comprises an apparatus for assessing the threat status of the liquid product. The apparatus comprises an input, a processing unit and an output and is operative for assessing the threat status of a liquid product in accordance with the above-described method. The system further comprises a display screen in communication with the output of the apparatus for visually conveying to an operator the assessed threat status of the liquid product based on information released by the apparatus.

In accordance with another broad aspect, the present invention provides a method for assessing a threat status of a liquid product at a security checkpoint. The liquid product is comprised of a bottle holding a liquid, wherein the bottle is at least partially filled with liquid. The method comprises performing an X-ray scan of the liquid product using an X-ray imaging apparatus to obtain X-ray image data associated with the liquid product. The method also comprises processing the X-ray image data to derive information conveying a level of fill of the bottle and determining the threat status of the liquid product at least in part based on the level of fill of the bottle. The method further comprises releasing information conveying the determined threat status of liquid product.

In accordance with another broad aspect, the present invention provides a method for assessing a threat status of a liquid product at a security checkpoint. The liquid product is comprised of a bottle holding a liquid, wherein the bottle is at least partially filled with liquid. The method comprises receiving X-ray image data associated with the liquid product, the X-ray image data being derived by performing an X-ray scan of the liquid product using an X-ray imaging apparatus. The method also comprises processing the X-ray image data to derive location information associated with a meniscus formed by the liquid in the bottle and processing the X-ray image data in combination with the location information associated with the meniscus formed by the liquid in the bottle to derive path length data. The path length data conveys an estimated length of a path followed by X-rays through the liquid held in the bottle. The method further comprises processing the X-ray image data in combination with the path length data to determine the threat status of the liquid product and releasing information conveying the determined threat status of the liquid product.

In a specific example of implementation, the method comprises receiving X-ray image data associated with the liquid product, wherein the X-ray image data is obtained using a multi-view X-ray machine. The X-ray image data conveys a first X-ray image of the liquid product taken by subjecting the liquid product to X-rays in a first orientation and a second X-ray image of the liquid product taken by subjecting the liquid product to X-rays in a second orientation. The method comprises processing the X-ray image data corresponding to the first X-ray image of the liquid product to derive estimated location information associated with the meniscus formed by the liquid in the bottle. The method also comprises processing the X-ray image data corresponding to the second X-ray image of the liquid product and the estimated location information associated with the meniscus obtained based on the X-ray image data corresponding to the first X-ray image to derive adjusted location information associated with the meniscus. The method further comprises deriving the path length data at least in part based on the adjusted location information associated with the meniscus formed by the liquid in the bottle.

In accordance with another broad aspect, the invention provides a computer readable storage medium storing a program element suitable for execution by a computing apparatus for assessing a threat status of a liquid product at a security checkpoint. The liquid product is comprised of a bottle holding a liquid, wherein the bottle is at least partially filled with liquid. The computing apparatus comprises a memory unit, a processor operatively connected to the memory unit. The program element, when executing on the processor, is operative for assessing the threat status of a liquid product in accordance with the above-described method.

In accordance with yet another broad aspect, the invention provides an apparatus for assessing a threat status of a liquid product at a security checkpoint. The liquid product is comprised of a bottle holding a liquid, wherein the bottle is at least partially filled with liquid. The apparatus comprises an input, a processing unit and an output and is operative for assessing the threat status of a liquid product in accordance with the above-described method.

In accordance with a further broad aspect, the invention provides a system suitable for assessing a threat status of a liquid product at a security checkpoint. The liquid product is comprised of a bottle holding a liquid, wherein the bottle is at least partially filled with liquid. The system comprises an inspection device for performing an X-ray inspection on the liquid product using penetrating radiation to generate an X-ray image of the liquid product. The system also comprises an apparatus for assessing the threat status of the liquid product. The apparatus comprises an input, a processing unit and an output and is operative for assessing the threat status of a liquid product in accordance with the above-described method. The system further comprises a display screen in communication with the output of the apparatus for visually conveying to an operator the assessed threat status of the liquid product based on information released by the apparatus.

In accordance with yet a further broad aspect, the invention provides an apparatus for assessing a threat status of a liquid product at a security checkpoint. The liquid product is comprised of a bottle holding a liquid, wherein the bottle is at least partially filled with liquid. The apparatus comprises means for receiving X-ray image data associated with the liquid product, the X-ray image data being obtained by performing an X-ray scan of the liquid product using an X-ray imaging apparatus. The apparatus also comprises means for processing the X-ray image data to derive information conveying a level of fill of the bottle and means for determining the threat status of the liquid product at least in part based on the level of fill of the bottle. The apparatus further comprises means for releasing information conveying the determined threat status of liquid product.

In accordance with another broad aspect, the invention provides a method for assessing a threat status of a liquid product at a security checkpoint, the liquid product being comprised of a bottle holding a liquid, wherein the bottle is at least partially filled with liquid. The method comprises determining if the bottle holding the liquid has a level of fill below a threshold level of fill. In response to the level of fill of the bottle falling below the threshold level of fill, the method includes rejecting the liquid product as a being a potential threat. In response to the level of fill of the bottle being at least at the threshold level of fill, the liquid product is screened using an X-ray machine to derive the threat status of the liquid product.

Other aspects and features of the present invention will become apparent to those ordinarily skilled in the art upon review of the following description of specific embodiments of the invention in conjunction with the accompanying Figures.

BRIEF DESCRIPTION OF THE DRAWINGS

A detailed description of examples of implementation of the present invention is provided herein below with reference to the following drawings, in which:

FIG. 5h is a cutaway side view of the bottle shown in FIG. 5a filled with liquid up to a second level of fill different from the first level of fill and maintained in an inclined position in accordance with a non-limiting example of implementation of the invention;

FIGS. 7a and 7b are diagrammatic representations of bottles partially filled with liquid and depicting different location meniscus;

FIG. 8 depicts a relationship between different coordinate spaces according to a non-limiting example of implementation of the invention;

Figure 1:
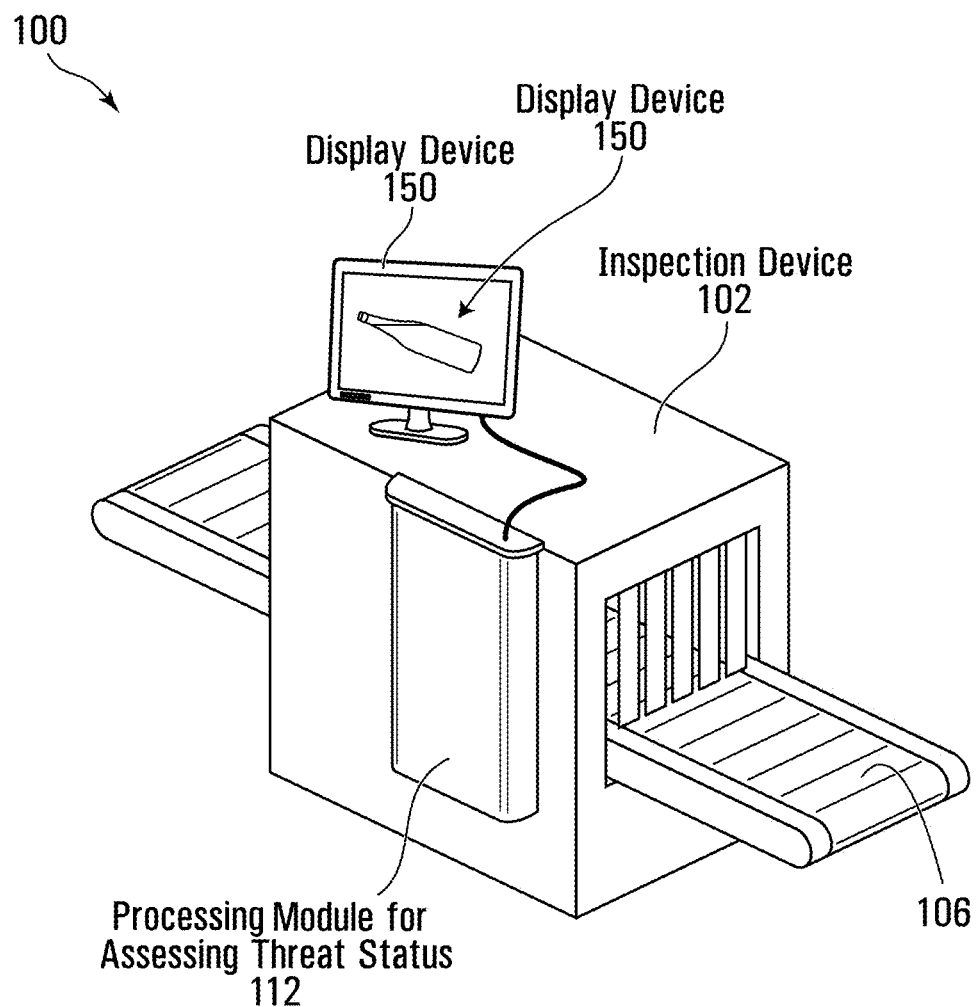
FIG. 1 shows a system for assessing the threat status of a liquid product at a security checkpoint in accordance with a specific example of implementation of the invention.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

Specific examples of implementation of the invention will now be described with reference to the figures. For the purpose of this description, the objects for which the threat status is to be assessed include liquid products comprised of a bottle holding a liquid, wherein the bottle is at least partially filled with liquid. It will be appreciated that, in addition to inspecting liquid products to assess their threat status, other embodiments of the invention may further be configured to assess the threat status of other types of objects. For example, embodiments of the invention may be configured to detect the presence of weapons or prohibited objects based on shape. Such additional functionality may be implemented in accordance with any suitable methods known in the art and will not be described further here.

For the purpose of the present description, a "bottle holding a liquid" refers to the combination of a body of liquid and the container in which the liquid is contained. For the purposes of this specification, "liquid" refers to a state of matter that is neither gas nor solid, that generally takes the shape of the container in which it is put and has a characteristic readiness to flow. Heterogeneous liquids would also be encompassed by such a definition.

In addition, a "bottle" refers to the container in which the liquid is contained. Although the term "bottle" typically refers to a cylindrical container that is used to contain liquids (namely beverages), a bottle in this specification refers to any enclosing structure that is made from a material that is suitable to hold the liquid contained within. Such containers include but are not limited to rigid containers, such as a glass bottle or metal (e.g. Aluminum) containers, as well as semi-rigid containers, such as a bottle made of polyvinyl chloride (PVC), polyethylene or of similar flexible materials. The bottle may be of any shape including generally cylindrical bottles, such as those used for beverages (e.g. a wine bottle or a can of a soft drink), square bottles used for beverage and non-beverage liquids (e.g. a carton of milk or fruit juice), elliptical bottles, rectangular bottles as well as bottles of any other suitable shapes. Each bottle has a transverse dimension and a longitudinal dimension that defines an overall size suitable to be carried in hand-carried luggage that is allowed onboard a commercial aircraft. In the case of cylindrical bottles, the transverse dimension is defined by the diameter of the bottle, which may differ between a bottom end and a tapered top end of the bottle. For example, bottles containing wine traditionally have a larger circumference at their bottom end that narrows as the bottle tapers at the top end. Without intent of being hound by any specific definition, bottles filled with liquid of an overall size suitable for transport in hand-carried luggage allowed onboard a commercial aircraft are those that have a transverse dimension that is less than 5 inches, preferably less than 4 inches, and most preferably less than 3 inches. However, these dimensions are merely guidelines and may vary depending on the rules and regulations enforced for such articles by local, national and international transportation organizations.

Referring now to the figures, shown in FIG. 1 is a screening system 100 suitable for assessing the threat status of a liquid product at a security checkpoint in accordance with a specific example of implementation of the present invention.

As depicted, the system 100 includes an inspection device 102 for scanning objects, a processing module 112 for processing data generated by the inspection device 102 and a display device 150 for visually conveying information to a security operator, the information being derived by the processing module 112 and pertaining to the objects being scanned by the inspection device 102.

More specifically, the inspection device 102 is adapted for scanning a liquid product using penetrating radiation to generate X-ray data conveying an X-ray image of the liquid product. The processing module 112 receives the X-ray data from the inspection device 102 and processes that data to derive information related to the threat status of that liquid product. In accordance with a first approach, the processing module 112 processes the X-ray image data to derive information conveying a level of fill of the bottle and to determine the threat status of the liquid product at least in part based on the level of fill of the bottle. In accordance with a second approach, which may be used concurrently with or independently from the first approach, the processing module 112 processes the X-ray image data to derive location information associated with a meniscus formed by the liquid in the bottle. The processing module 112 then processes the X-ray image data in combination with the location information associated with the meniscus formed by the liquid in the bottle to derive path length data, the path length data conveying an estimated length of a path followed by X-rays through the liquid held in the bottle. The processing module then processes the X-ray image data in combination with the path length data to determine the threat status of the liquid product. Specific examples of the manner in which the threat status of the liquid product can be determined will be described later on in the specification.

Once the threat status of the liquid product has been determined, the processing module 112 then releases information conveying the determined threat status. The display device 150, shown in the figure as a display screen, visually conveys to an operator the determined threat status of the liquid product based on the information released by the processing module 112.

Advantageously, the system 100 provides assistance to the human security personnel in assessing the threat status of a liquid product, including full bottles and partially filled bottles, during security screening.

The components of the system 100 depicted in FIG. 1 will now be described in greater detail.

Display Device 150

The display device 150 may be any device suitable for visually conveying information to a user of the system 100. The display device 150 may be part of a computing station, as shown in FIG. 1, may be part of a centralized security station and located remotely from the inspection device 102 or may be integrated into a hand-held portable device (not shown) for example. In another specific example of implementation, the display device 150 includes a printer adapted for displaying in printed format information related to the determined threat status of the liquid product under inspection. The person skilled in the art will readily appreciate, in light of the present specification, that other suitable types of output devices may be used in alternative examples of implementation of the present invention.

In a specific example of implementation, the display device 150 displays to a user of the system 100 a graphical user interface conveying the determined threat status of the liquid product based on the information released by the processing module 112. The graphical user interface (GUI) may also provide functionality for permitting interaction with a user.

The specific manner in which the information is visually conveyed to a human operator may vary from one implementation to the other.

In a first example of implementation, the information conveying the determined threat status of the liquid product conveys the threat status in terms of a level of threat. The level of threat may be represented as an alpha numeric character (SAFE/UNSAFE/UNKNOWN), a color indicator (e.g. RED for unsafe; GREEN for safe and YELLOW for UNKNOWN) and/or using any other suitable manner of conveying a level of threat.

In a second example of implementation, the information conveying the determined threat status of the liquid product provides information as to the nature of the liquid product being screened. For example, the GUI may indicate that the liquid product may be water, orange juice, hydrogen peroxide and so on. Optionally, when indicating the nature of the liquid product, a level of confidence in the determination may be displayed. For example, the GUI may indicate that the liquid product is likely to be water with a level of confidence of 80%.

In a third example of implementation, the information conveying the determined threat status of the liquid product provides information as to the level of fill of the liquid product. For example, the information may convey that the bottle is X % full. In situations where X % is less then a threshold level of fill, the information displayed to the user may further convey that since X % is less then the threshold filled level, the bottle has been classified as UNSAFE irrespective of its content.

It will be readily apparent to the person skilled in the art that other types of information may be displayed by display device and that the examples provide above were provided for the purpose of illustration only.

Inspection Device 102

In a specific example of implementation, the inspection device 102 is in the form of an X-ray machine typical of the type of device used to scan luggage at security checkpoints within airports and other transportation locations. The X-ray machine may be a single view x-ray machine or a multi-view x-ray machine. For the purpose of simplicity, the present description will primarily focus on implementations in which the X-ray machine is of a single-view type. Variants of the invention taking advantage of the multiple X-ray images generated by multi-view X-ray machines will also be presented.

The inspection device 102 will now be described in greater detail with reference to FIG. 2. As depicted, the inspection device 102 includes a scanning area 104, a conveyor belt 106, an X-ray source 108 and an array of X-ray detectors 110. The inspection device 102 performs an X-ray inspection on a liquid product using penetrating radiation in the form of X-rays to generate X-ray image data associated with the liquid product.

The scanning area 104 (also referred to as scanning tunnel) is defined by an enclosed void between the X-ray source 108 and the array of X-ray detectors 110, in which the objects to be scanned are subjected to penetrating radiation, such as X-rays. The scanning area 104 is typically horizontally oriented and is dimensioned both vertically and horizontally to accommodate the types of objects to be scanned, including articles of hand-carried luggage allowed onboard a commercial aircraft, such as handbags, backpacks, briefcases and shopping bags, among others. The scanning area 104 is centrally traversed by a conveyor belt 106 that is used to convey objects to be scanned both into and out of the scanning area 104 and is described below.

The articles to be scanned can be placed either directly on the conveyor belt 106 or in one or more trays that are then placed on the conveyor belt 106.

The conveyor belt 106 is a horizontally-oriented continuous belt of material arranged in an endless loop between two terminal rollers. The belt 106 has an exterior surface on which objects or trays containing the objects to be scanned are placed, as well as an interior surface within which the terminal rollers (as well as other guide rollers anti/or supports) lie.

The width of the conveyor belt 106 is sufficient to accommodate the placement of trays within which the objects to be scanned are placed, while its overall length is sufficient to create an endless loop whose length includes:

A pre-scanning area that lies before the scanning area 104, where the objects to be scanned are placed on the belt 106;

The scanning area 104, where the objects being scanned are subjected to penetrating radiation (i.e. X-rays); and A post canning area that lies after the scanning area 104, where the objects that have been scanned emerge after being subjected to penetrating radiation. It is in that area that a user can pick up his or her objects after the security screening operation is completed.

It is worth noting that the terminal rollers constituting the end points of the conveyor belt 106 at the pre-scanning and post-scanning areas may be connected to motors (not shown) that allow an operator to move the belt 106 forwards or backwards to displace the objects to be scanned between different areas of the X-ray inspection device 102.

The X-ray source 108 is the source of penetrating radiation (in this case, X-ray radiation). The X-ray source 108 is located opposite to the array of X-ray detectors 110 so that X-rays emitted by the source 108 pass through the objects that are located on the conveyor belt 106 and are detected by the array of X-ray detectors 110 as a result. In a non-limiting example, the inspection device 102 is a dual-energy X-ray scanner and the x-ray source 108 emits x-rays at two distinct photon energy levels, either simultaneously or in sequence. Example energy levels include 50 keV (50 thousand electron-volts) and 150 keV, although persons skilled in the art will appreciate that other energy levels are possible.

The array of X-ray detectors 110 detects the penetrating radiation (i.e. X-rays) that was emitted by the X-ray source 108 and that penetrated the objects to be scanned. The array of X-ray detectors 110 is located opposite to the X-ray source 108 so that X-rays that are emitted by the source 108 pass through the objects that are located on the conveyor belt 106 and are detected by the array 110.

Processing Module 112

The processing module 112 is in communication with the inspection device 102 and receives the X-ray image data output by the array of X-ray detectors 110. In the example depicted in FIGS. 1 and 2, the processing module 112 is shown as a component external to the inspection device 102. It will be appreciated that, in alternate example of implementation of the system 100, the functionality of processing module 112 may be integrated within the inspection device 102.

The processing module 112 uses the X-ray data output by the array of X-ray detectors 110 of the inspection device 102 to generate an X-ray image of the contents being scanned. The generated X-ray image is then processed and/or analyzed farther by human or automated means, as will be shown below, in a non-limiting example of implementation, attenuation information conveyed by the X-ray image data generated by the inspection device 102 is processed to generate an X-ray image in which different shades of gray are used to convey different levels of attenuation of the X-rays.

Figure 3:
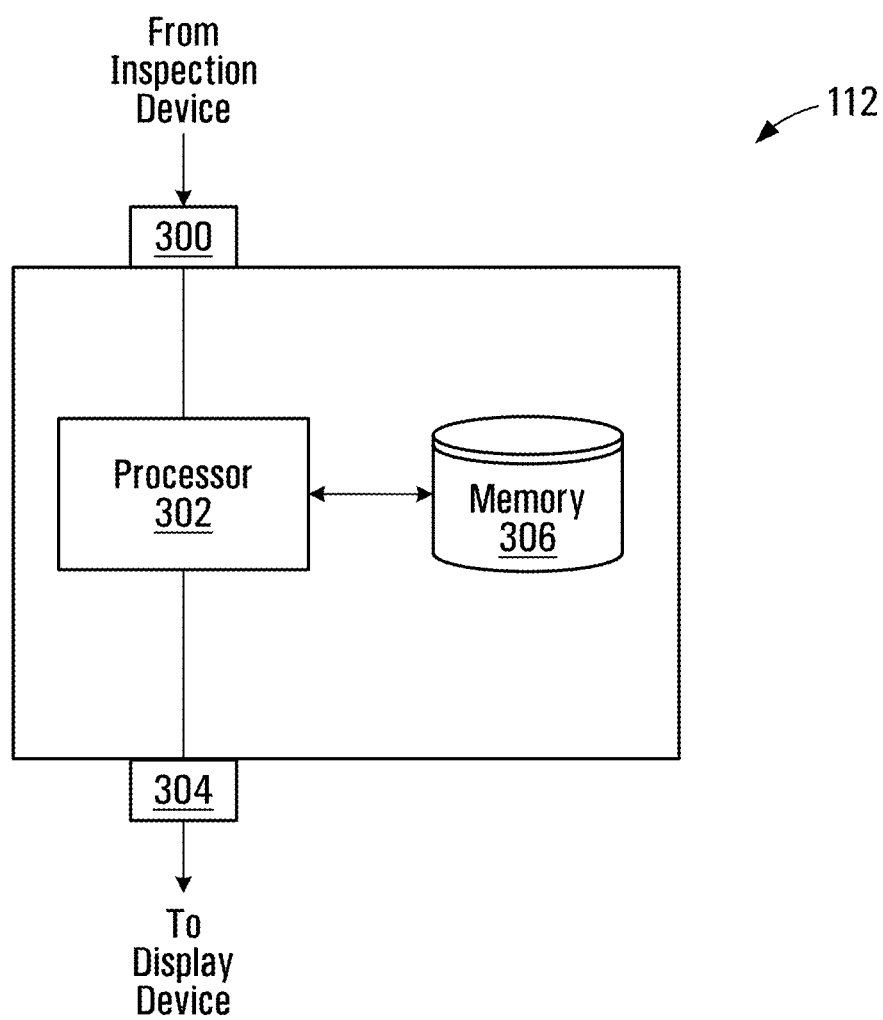
FIG. 3 is a block diagram of a processing module for assessing the threat status of a liquid product suitable for use in the system depicted in FIG. 1 in accordance with a specific example of implementation of the invention.

A specific example of implementation of the processing module 112 is depicted in FIG. 3 of the drawings. As shown, the processing module 112 includes an input 300 in communication with the inspection device 102 for receiving there from X-ray data, a processor 302 in communication with the input 300, a memory 306 storing data for use by the processor 302 and an output 304 in communication with the display device 150 (shown in FIG. 1) for releasing information derived by the processor 302.

The processor 302 implements a process for assessing the threat status of a liquid product unit based on the X-ray data received at input 300 from the inspection device 102. Results of the threat status assessment are then released at output 304. Specific examples of processes for assessing the threat status of a liquid product that may be implemented by processor 302 will be described later on in the present specification.

The Level of Fill of a Bottle and the Meniscus

Prior to describing the process by which the threat status of a liquid product, a short description on impacts of the level of fill of a bottle on the determination of the characteristics of the liquid held by the bottle based on an X-ray image will be described for the purpose of facilitating the reader's understanding.

Generally speaking, the threat status of a bottle filled with liquid is based in part on X-ray attenuation information extracted from the X-ray image data and an estimated length of a path travelled by X-ray through the liquid in the bottle. The closer the estimate path length is to the actual length of the path travelled by X-rays through the body of liquid in the bottle, the more accurate the nature of the liquid in the bottle can be derived and therefore a more accurate assessment of its threat status can be made.

Since bottles are typically not filled to their full capacity, there is usually a meniscus that can interfere with the X-ray scanning. In situations in which the bottle being screened is completely full, or nearly completely full, the meniscus formed by liquid in the bottle being screened will be very small and will have minimal impact on the determination of the characteristics of the liquid held by the bottle (e.g. the effective atomic number ($Z_{eff}$ number), the density and/or linear attenuation coefficient) and the ensuing assessment of the threat status of the liquid product under inspection. However as the level of fill of the bottle diminishes, the impact of meniscus on the determination of the characteristics of the liquid held by the bottle, and hence the assessment of the threat status of the liquid product under inspection, increases and taking the meniscus into account will increase the accuracy of the threat assessment.

As can be observed, when a bottle is placed horizontally on the tray, the meniscus is likely to spread, and (depending on the size of the meniscus) an air layer may be created. The size of such an air layer is determined by the degree to which the bottle has been filled: a full bottle will have a smaller meniscus while a bottle filled partially will have a larger meniscus. In certain cases, the air layer created by the meniscus can extend above the entire body of liquid, which can lead to an inaccurate path length being obtained if the characteristics of the meniscus are not taken into account. For example, due to the presence of an air layer, the path length through the liquid body may be shorter than the distance between the bottle walls (the transverse dimension of the void space within the bottle).

It can also be observed that by setting a bottle holding liquid in an inclined position, the meniscus will tend to migrate toward one of the extremities of the bottle.

For the purpose of simplicity, examples presented in the present application will describe embodiments in which the bottle holding liquid is in an inclined position. Embodiments in which the bottles are placed horizontally during inspection will become readily apparent to the person skilled in the art in light of the present description.

Figure 5A:
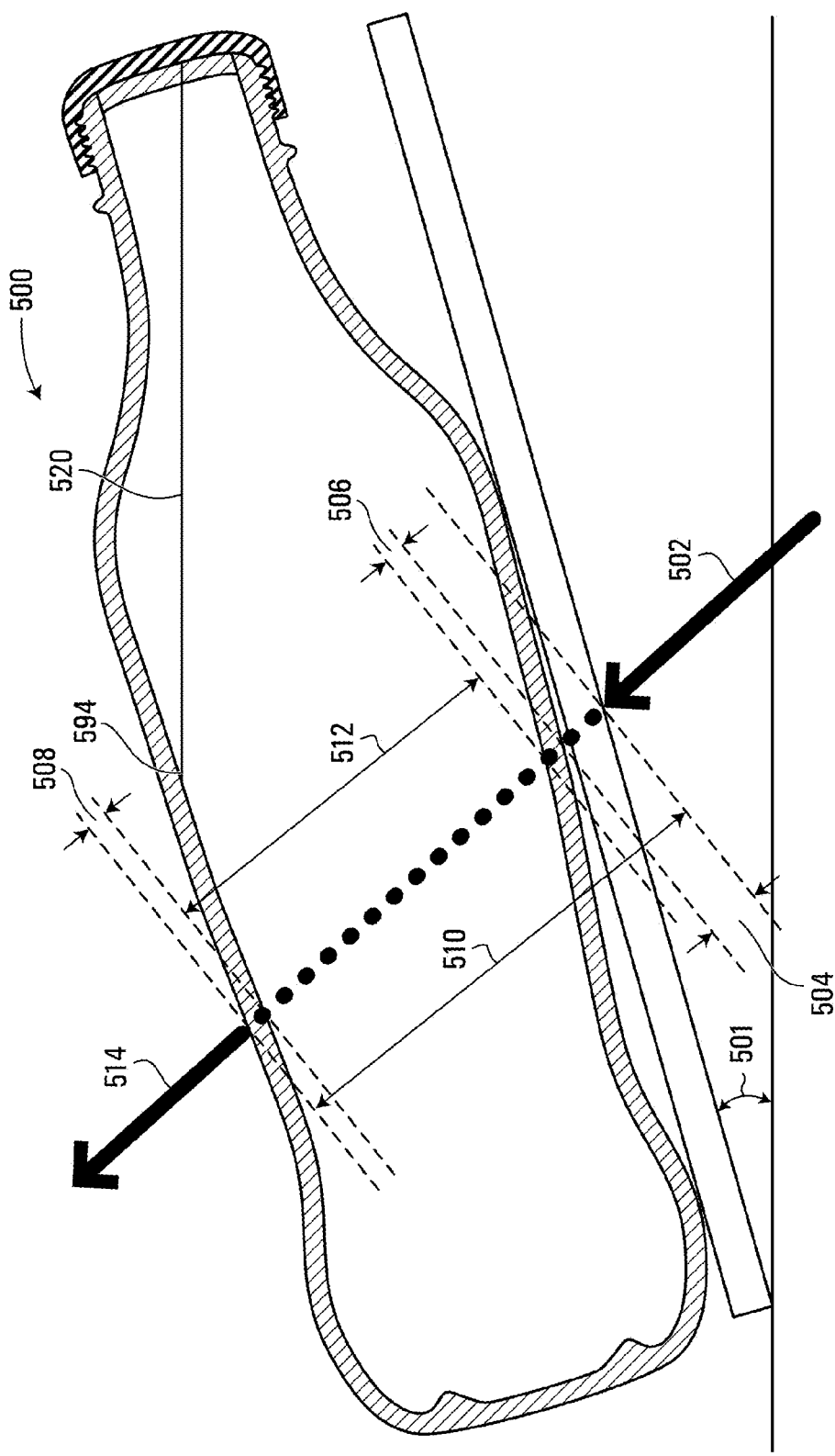
FIG. 5a is a cutaway side view of a bottle partially filled with liquid up to a first level of fill and maintained in an inclined position in accordance with a non-limiting example of implementation of the invention.

FIGS. 5a and 5b show a side cutaway view of a bottle 500 partially filled with liquid in an inclined position. With respect to these figures, the bottle 500 is generally inclined at an angle 501 relative to a generally horizontal plane. For the purpose of this example, the angle 501 is achieved by positioning the bottle on a tray having an inclined bottom surface and an angle of 501.

FIGS. 5a and 5b also show a path taken by a ray of penetrating radiation (i.e. an X-ray) through the bottle. The X-ray enters the bottle 500 at location 502, travels through the bottle walls and the bottle contents, and emerges from the bottle at location 514. The angle between the X-ray and the longitudinal axis of the bottle of liquid can be derived using simple trigonometry since the angle 501 is known and the orientation of the X-ray is also known.

As can be seen, as the X-ray travels from the X-ray source to the X-ray detectors (not shows), the X-ray is attenuated by not only the liquid in the bottle but by a supporting structure (such as a tray and/or conveyor belt) holding the bottle and the side walls of the bottle as well. Segment 510 between the locations 502 and 514, herein referred to as the combined segment 510, is a combination of the following segments:

segment 504 through the supporting structure (for example a tray);

segments 506 and 508 through the side walls of the bottle; and segment 512 through the inside portion of the bottle 500.

The lengths of segments 504, 506 and 508 may be derived based on the thickness of the supporting structure (tray material) and the bottle side walls, both of which may be known or may be derived using other image analysis techniques known in the art. Similarly, the length of the combined segment 510 may be obtained based on geometrical information associated with the bottle obtained based on the X-ray image and/or based on certain geometrical assumptions as to the shape of the bottle and obtained (symmetry, shape of the bottom of the bottle, reference database of bottle shapes, etc. . . . ). As a result, the length of the segment 512 may be determined by subtracting the lengths 504, 506 and 508 from the length of combined segment 510.

As can be observed in FIG. 5*a*, the position of the meniscus 520 is such that the length of the path segment 512, which is the length of the path through the inside portion of the bottle 500, corresponds to the length of the path taken by the X-ray passing entirely through the liquid within the bottle. As such, the length of the path segment 512 can be used with other information, such as X-ray attenuation information obtained from an X-ray image of the bottle holding the liquid, to derive characteristics of the liquid in the bottle including, for example, density, the effective atomic number ($Z_{eff}$ number) and/or linear attenuation coefficient according to well known methods. Known attenuation information, such as the attenuation attributed to the tray, conveyor belt and optionally the walls of the bottle 500 can also be taken into account to compensate the attenuation information in the X-ray image data when deriving characteristics of the liquid in the bottle.

If we now consider FIG. 5*b*, we note that the position of the meniscus 520' is such that the length of the path segment 512 includes a first component 592 corresponding to the length of the path taken by the X-ray passing through the liquid within the bottle but also includes a second component 590 corresponding to the length of a path taken by the X-ray in a layer of air above the meniscus. As a result, the determination of the length of the path taken by the X-ray through the body of liquid (in other words component 592), should take into account the location and characteristics of the meniscus.

As can be observed from FIGS. 5*a* and 5*b*, since the meniscus is a generally horizontal flat surface aligned with the surface of the conveyor belt, the level of meniscus 520 520' can be determined by identifying the location of the point (594 in FIGS. 5*a* and 594' in FIG. 5*b*) at which the meniscus is in contact with the wall of the bottle. Once of the location of the meniscus is known, it can be used in determining a more accurate path length taken by x-ray through the liquid, in particular in situations where the level of fill of the bottle is such that there is a layer of air above the meniscus (as in FIG. 5*b*).

The location information associated with the meniscus may include various components such as:
  The height of the meniscus relative to the conveyor belt of the inspection device 102;
  The location of the point (594 in FIGS. 5*a* and 594' in FIG. 5*b*) at which the meniscus is in contact with the wall of the bottle
  Distance 590 in FIG. 5*b*

It is to be appreciated that any method suitable for determining the location of the meniscus, including the level (height) of the meniscus and/or the location of the point (594 in FIGS. 5*a* and 594' in FIG. 5*b*) at which the meniscus is in contact with the wall of the bottle may be used. Specific approaches for determining the approximate location of the point (594 in FIGS. 5*a* and 594' in FIG. 5*b*) and the level of the meniscus based on an x-ray image of the bottle will be described later on in the specification with reference to FIGS. 16*a*, 16*b* and 16*c*.

As can be observed from FIGS. 5*a* and 5*b*, having knowledge of location information associated with the meniscus and information pertaining to the geometry of the bottle under inspection, the level of fill of the bottle 500 can be derived using well-known methods.

As can also be observed from FIGS. 5*a* and 5*b*, having knowledge of location information associated with the meniscus and information pertaining to the geometry of the bottle under inspection, the length of the path of an X-ray through a continuous body of liquid (segment 512 in FIG. 5*a* and segment 592 in FIG. 5*b*) can be obtained and used according to well-known methods to derive characteristics of the liquid held by the bottle (e.g. density, effective atomic number ($Z_{eff}$ number) and/or linear attenuation coefficient) and the ensuing assessment of the threat status of the liquid product under inspection.

Process Implemented by System 100

Figure 4A:
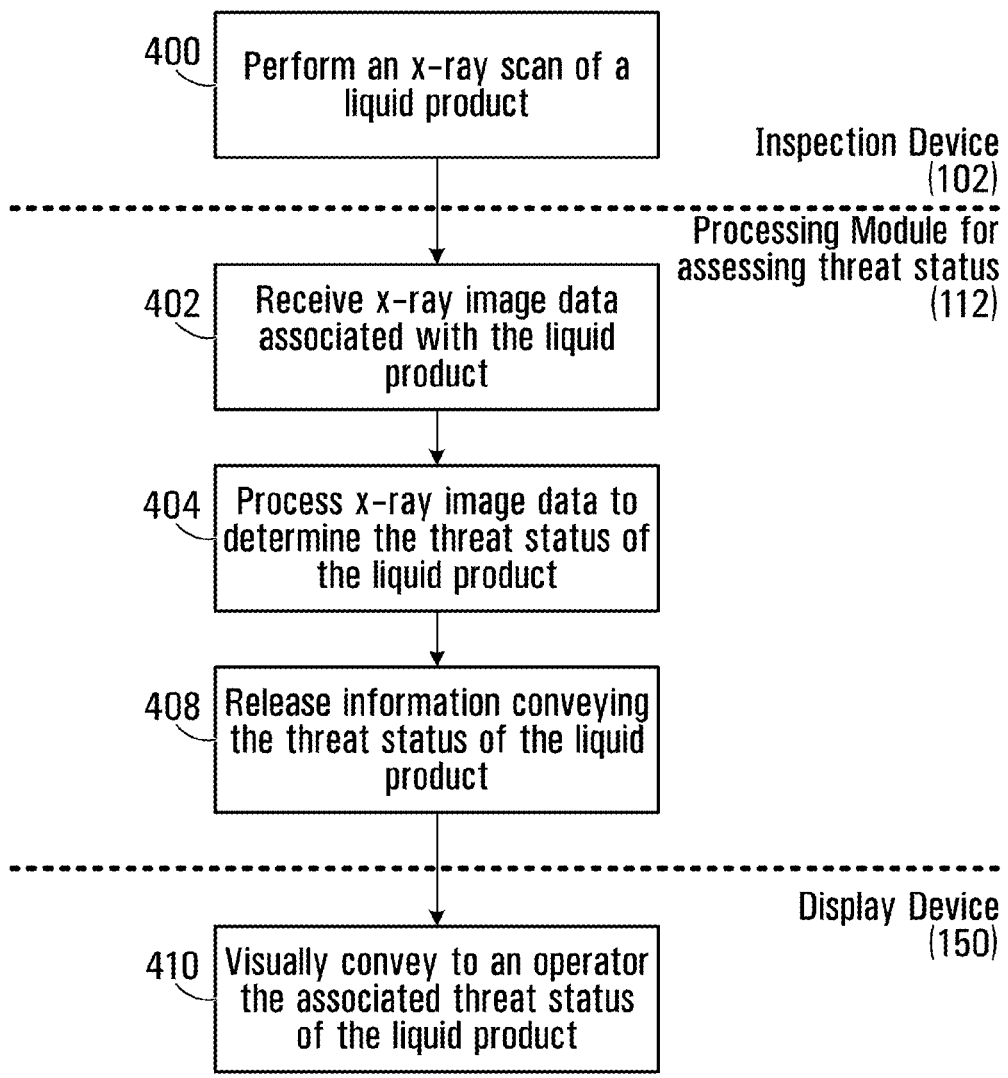
FIGS. 4a and 4b are flow diagrams of a process implemented by the system depicted in FIG. 1 in accordance with a specific example of implementation of the invention.

A specific example of a process implemented by the system 100 (shown in FIG. 1) will now be described with reference to FIG. 4A.

As shown, at step 400 an X-ray scan of a liquid product to be screened is performed by the inspection device 102 (shown in FIG. 1) to obtain X-ray image data associated with the liquid product.

In a first non-limiting example, the liquid product is placed directly on the conveyor belt of the inspection device 102 or is placed on a tray which is then placed on the conveyor belt of the inspection device 102.

Figure 6:
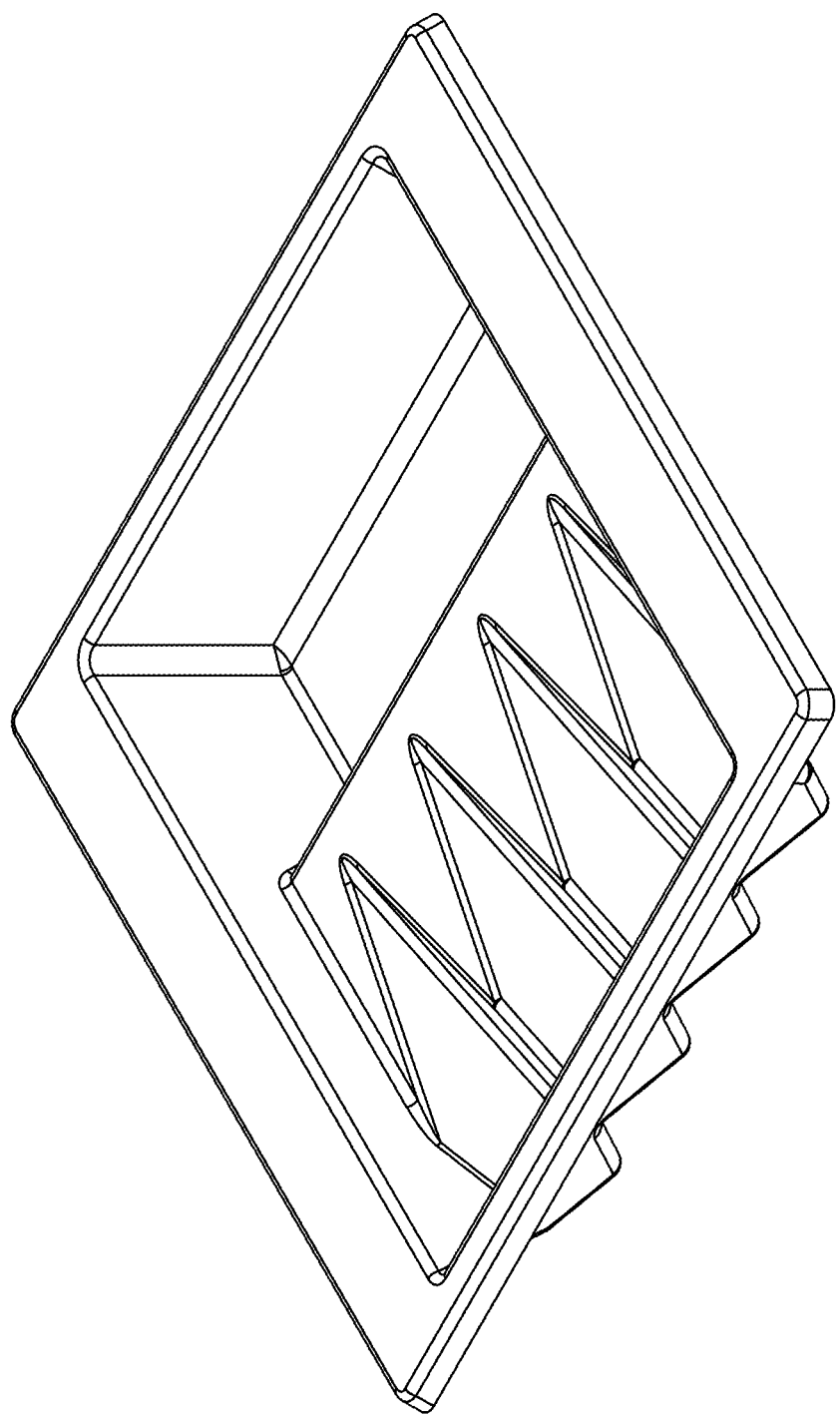
FIG. 6 is a top perspective view of a tray for positioning a bottle in an inclined position during X-ray inspection according to a non-limiting example of implementation of the invention.

In a second non-limiting example, the liquid product is placed on a tray having an inclined bottom surface and including retaining member for preventing the liquid product from being displaced during inspection. For example, a tray of the type depicted in FIG. 6 may be used for that purpose. In a specific example of implementation, the bottom surface of the tray longitudinal axis forms an angle to the horizontal plane in the range from about 5° to about 40°, preferably in the range from about 5° to about 30°, and preferably in the range from about 10° to about 20°. In a specific non-limiting practical implementation, the angle is between about 10° and about 15°.

The person skilled in the art will appreciate that it is desirable to maintain the stability of the liquid product during the scanning operation in order to improve the accuracy of the threat detection process. Should the liquid product be allowed to roll or otherwise move on the surface of the tray or the conveyor belt, (especially when the bottle is of a circular cross-sectional shape, which would promote such movement) the X-ray image may be taken while the bottle is in motion. This motion may produce corrupted X-ray image data that may lead to a false identification (i.e. a non-threatening liquid being assessed as a threat and vice versa) or require that another X-ray image be taken before any analysis is performed. As such, mechanisms for positioning the liquid product and preventing it from being displaced during inspection may be used when scanning the liquid product. The reader is invited to refer to the following document for examples of mechanisms for positioning a liquid product:
  PCT International Patent Application serial number PCT/CA2008/002025 filed in the Canadian Receiving Office on Nov. 17, 2008 by Michel Roux et al. and presently pending.

The contents of the above mentioned document are incorporated herein by reference.

Figure 2:
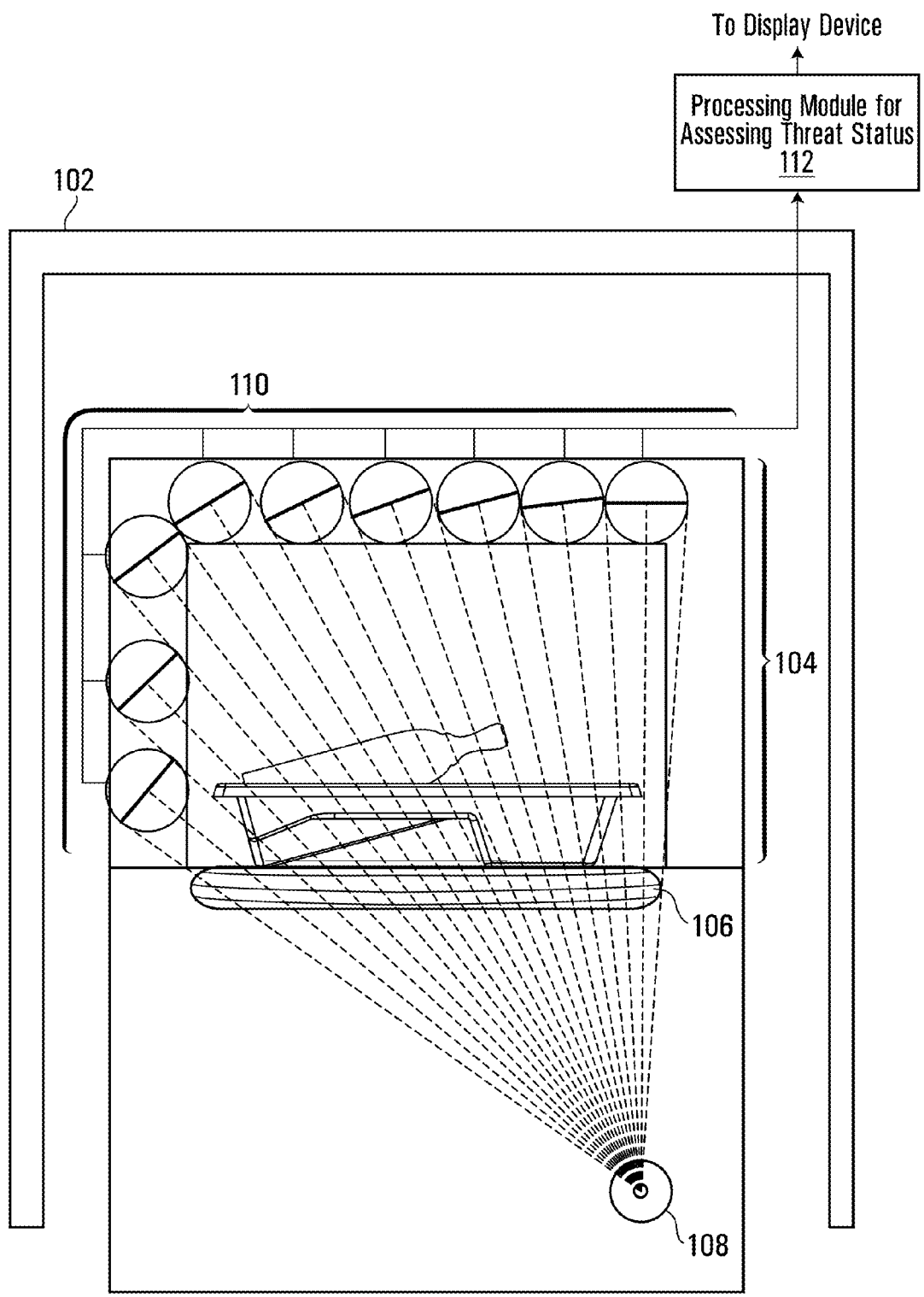
FIG. 2 is a diagrammatic representation of an inspection device suitable for use in the system depicted in FIG. 1 in accordance with a specific example of implementation of the invention.
Figure 9A:
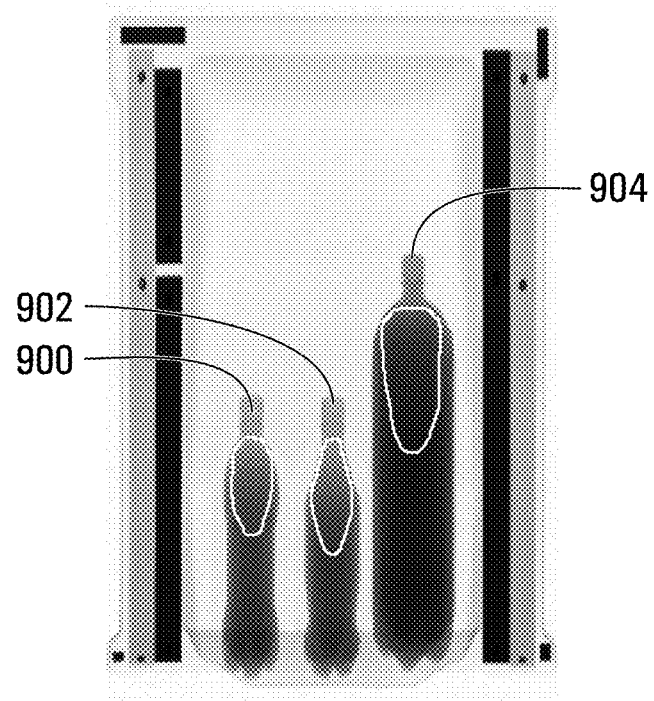
FIG. 9a is an X-ray image of three (3) bottles each at least partially filled with liquid in accordance with a specific example of implementation of the invention.

The liquid product having been placed either directly on the conveyor belt or on a tray is then displaced toward the scanning area 104 of the inspection device 102 (shown in FIG. 2). X-ray image data is then generated by the inspection device 102 by subjecting the liquid product to penetrating radiation. FIG. 9*a* is an X-ray image of three (3) bottles each at least partially filled with liquid derived from data generated by an inspection device in accordance with a specific example of implementation of the invention. In this figures, the meniscus for each bottle has been emphasized in this image for the purpose of illustration only.

At step 402, the X-ray image data generated by the inspection device 102 is received by the processing module 112.

At step 404, the processing module 112 processes the X-ray image data to determine the threat status of the liquid product scanned at step 400. Many different approaches may be taken for determining the threat status of the liquid product.

In accordance with a first approach, the processing module 112 processes the X-ray image data to derive information conveying a level of fill of the bottle and to determine the threat status of the liquid product at least in part based on the level of fill of the bottle.

In accordance with a second approach, which may be used concurrently with or independently from the first approach, the processing module 112 processes the X-ray image data to derive location information associated with a meniscus formed by the liquid in the bottle. The processing module 112 then processes the X-ray image data in combination with the location information associated with the meniscus formed by the liquid in the bottle to derive path length data, the path length data conveying an estimated length of a path followed by X-rays through the liquid held in the bottle. The processing module 112 then processes the X-ray image data in combination with the path length data to determine the threat status of the liquid product.

In accordance with a third approach, which may be used concurrently with or independently from the first and second approaches, the processing module 112 may implement a method for assessing the characteristics of liquids from the X-ray images of bottles of liquid of the types described in international patent application no. PCT/CA2007/001658, "Method and Apparatus for Assessing the Characteristics of Liquids", which was filed by Optosecurity Inc. et al. with the Canadian Receiving Office on Sep. 17, 2007 and was published on Mar. 27, 2008 under publication no. WO2008034232. The contents of the aforementioned document are incorporated herein by reference. Amongst others, the above referenced PCT application describes a method that can be implemented as software and/or hardware and that can be used in order to perform an analysis of X-ray image data in order to determine a threat status of a container. In particular, the method described makes use of X-ray attenuation information extracted from the X-ray image, which was obtained by subjecting the bottles filled with liquid to X-ray radiation, to determine if a bottle filled with liquid presents a threat or not.

Specific examples of the manner in which step 404 may be implemented will be described in greater detail below.

At step 408, the processing module 112 releases information conveying the threat status of the liquid product determined at step 404.

Following this, at step 410, the display device 150 (shown in FIG. 1) receives the information released by the processing modules and conveys this information in visual format, and optionally in audio format, to an operator.

Step 404

A specific approach for determining the threat status of the liquid product at step 404 will now be described with reference to FIG. 4B. It will be readily appreciated that other suitable approaches may be contemplated in alternative examples of implementation of the invention. Such alternative approaches will become apparent to the person skilled in the art in light of the present description.

As depicted, at step 440 the X-ray image data received from the inspection device 102 (shown in FIG. 1) is processed to derive geometric information associated with the bottle of the liquid product. The derived geometric information associated with the bottle may include one or more of the following elements:

Approximation of the bottle height;
Approximation of the bottle width;
Approximation of the bottle length;
Approximation of the profile of the bottle;
Presence or absence of certain surface features such as:
   Annular recesses on the body of the bottle and position of those annular recesses;
   Presence or absence of cap
Approximation of the position of the bottle in the tray
   Three-dimensional representation of the bottle The image processing performed to extract the features described above can be done using any suitable image processing technique known in the art.

In implementations in which the inspection device 102 (shown in FIG. 1) is a "single-view" type X-ray machine generating a two-dimensional image of the liquid product, image processing techniques allowing deriving three-dimensional information based on a two-dimensional image are used, in implementation in which the liquid product is positioned on a tray having a bottom surface with a known inclination, the angle made between a longitudinal axis of the bottle and a horizontal plane is used to derive the geometric information associated with the bottle. Assumptions based on the symmetry of the bottle holding the liquid as well as assumption regarding the inclination of the bottle for example in cases where the bottles are positioned at a known angle of inclination using a tray) may be used in order to assist in the extraction of geometric information associated with the bottle. More specifically, the person skilled in the art will appreciate that, although there may be some exceptions, most bottles have shapes exhibiting symmetrical properties. For instance, several bottles exhibit some level of rotational symmetry along their longitudinal axis. For example, the general three-dimensional shape of a bottle can be approximated by:

deriving the location and orientation of its longitudinal axis;
   deriving the extent (extremities of the bottle);
   deriving the shape of the profile of the bottle along one side of the longitudinal axis; and
   extrapolating all other points on the bottle by effecting a rotation of the profile of the bottle around the longitudinal axis.

Although the above approach assumes that the bottle has a generally circular cross-section, the person skilled in the art will readily appreciated that adaptations to account for bottles having generally elliptical, generally square and generally rectangular cross-section can also be made. In implementations in which the inspection device 102 (shown in FIG. 1) is a "multi-view" type X-ray machine generating multiple two-dimensional image of the liquid product, the multiple images may be used to obtain additional information as to the size, shape and positioning of the bottle. Several suitable methods for extracting geometric information from an image are known in the art of computer vision and as such will not be described in further detail here.

In a non-limiting example of implementation, a three-dimensional mathematical representation of the bottle under inspection is generated at step 440 based on the X-ray image data generated by the inspection device 102 (shown in FIG.

Figure 9B:
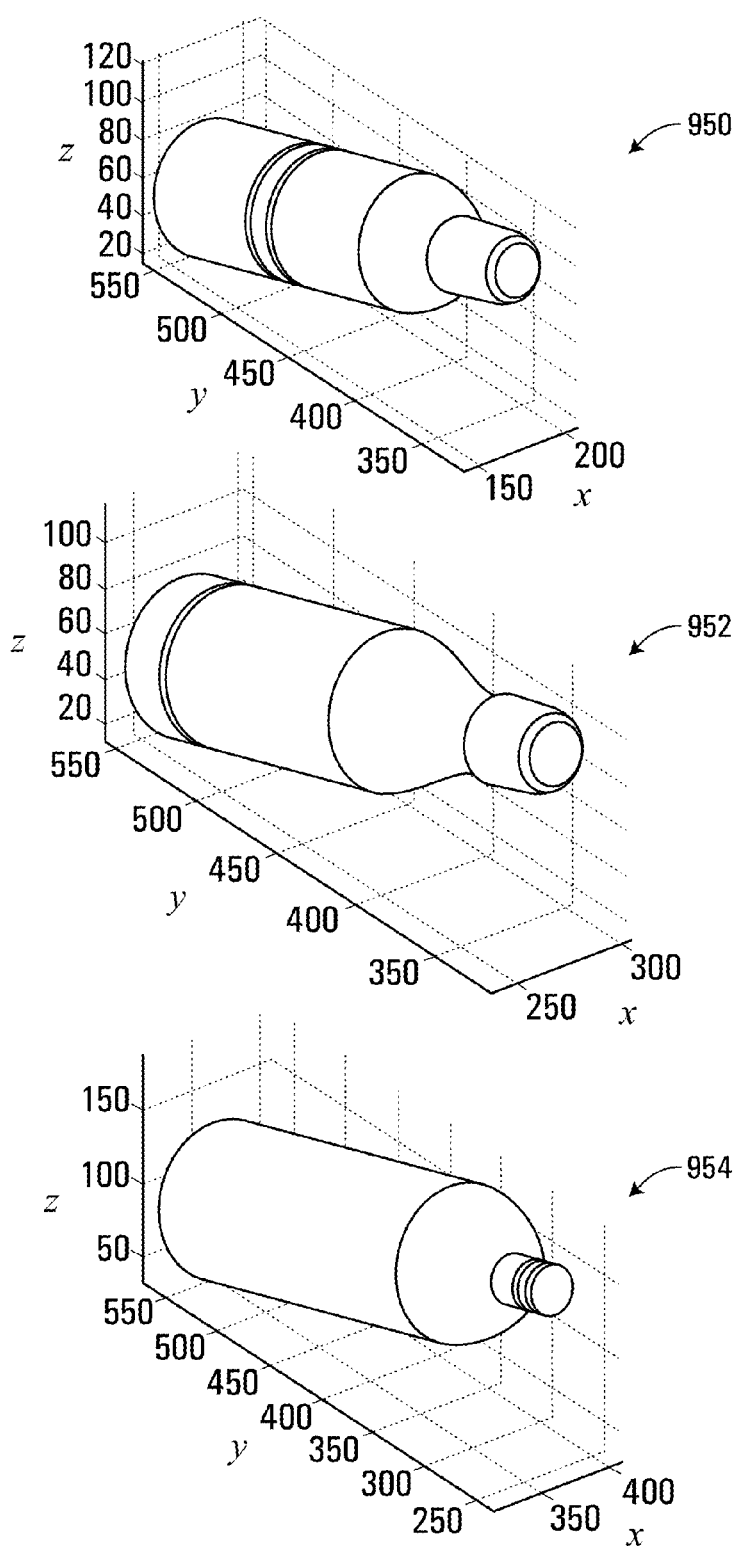
FIG. 9b shows visual representations of reconstructed 3-D images of the three (3) bottles depicted in the X-ray image of FIG. 9a in accordance with a specific example of implementation of the invention.

1). FIG. 9B of the drawings shows graphical three-dimensional mathematical representations 950 952 954, corresponding respectively to bottles 900 902 and 904 depicted in the X-ray images shown in FIG. 9A.

Once geometric information associated with the bottle of the liquid product has been obtained, the process proceeds to step 442.

At step 442, the X-ray image data is processed to derive location information associated with a meniscus formed by liquid in the bottle being screened. As described above, location information associated with the meniscus may include various components including but not limited to:

- The height of the meniscus relative to the conveyor belt of the inspection device 102
- The location of the point (594 in FIGS. 5a and 594' in FIG. 5b) at which the meniscus is in contact with the wall of the bottle Any method suitable for determining location information associated with the meniscus may be used. Specific approaches for determining location information associated with the meniscus will be described later on in the specification with reference to FIGS. 16a, 16b and 16c.

Once the location of the meniscus is known, it can be used in determining the level of fill of the bottle and/or a path length taken by x-ray through the liquid, in particular in situations where the level of fill of the bottle is such that there is a layer of air above the meniscus.

Therefore, following step 442, the process proceeds to steps 444 and 446 and/or 450 452 and 460.

At step 444, the level of fill of the bottle is derived at least in part based on the geometric information associated with the bottle, which was derived in step 440, and based on the location information associated with the meniscus, which was derived in step 442.

Any suitable method for deriving the level of fill of the bottle may be used without detracting from the spirit of the invention. In a non-limiting example, the volume of the bottle is derived based on the geometric information associated with the bottle according to well known methods. Similarly, the volume of the liquid in the bottle may be derived based on a combination of the geometric information associated with the bottle and the location information associated with the meniscus. Using the derived volume of the bottle and volume of liquid, the level of fill of the bottle may be derived by taking a ratio of the two volumes.

It will be appreciated that deriving the precise level of fill of a bottle, for example 25%, is not critical to the present invention. More specifically, the level of fill may be derived so that it is within a certain tolerance, for example 25% full±10%. Consequently, the level of fill of the bottle can be an approximate measure of the level of fill of the bottle rather than an exact measurement.

It will be appreciated that, in alternative embodiments, the derived level of fill of a bottle can simply indicate that the bottle has a level of fill above one or more certain pre-determined levels. For example, the derived level of fill may indicate that the bottle has a level of fill above 20%. This would encompass situations where the level of fill is 80% as well as cases where the level of fill is 30%.

At step 446, the level of fill of the bottle derived at step 444 is used as a factor to determine the threat status of the liquid product.

In a specific example of implementation, the level of fill of the bottle derived at step 444 is compared to a threshold level of fill. If the level of fill of the bottle is below the threshold level of fill, then a decision can be made to identify the liquid product as a threat irrespective of its content. The specific threshold level of fill used may vary from one implementation to the other and will generally depend on the amount of liquid necessary to be present in the bottle in order to perform a threat assessment having a sufficiently high rate of accuracy.

Figure 4B:
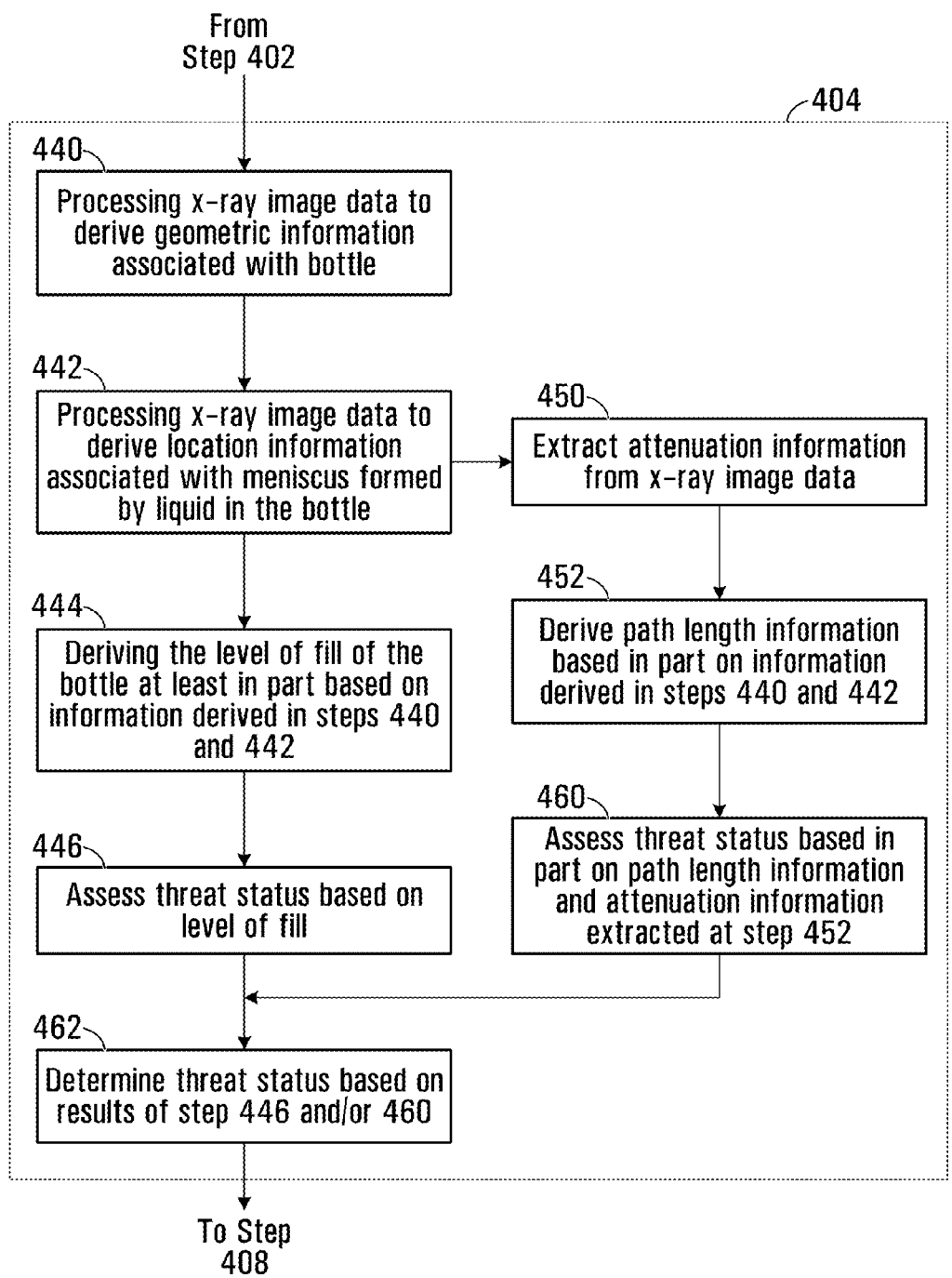

Generally speaking, the determined level of fill alone is not sufficient to identify a liquid product as "safe" and additional information will be used to complete the assessment such as for example the assessment performed in steps 450 452 and 460 in FIG. 4B.

Consequently, in a specific example of implementation after step 446, the liquid product will have been identified either as a being a "threat" or as being "undetermined and requiring further assessment". In cases where the liquid product has been identified as a threat based on the level of fill, steps 450 452 and 460 may be omitted.

In cases where the liquid product has been identified as being undetermined and requiring further assessment, the process continue with steps 450 452 and 460.

At step 450, the X-image data is processed to extract X-ray attenuation information associated with the liquid in the bottle. The X-ray attenuation information in the X-ray image may be processed to compensate it for an attenuation attributed to elements extraneous to the liquid in the bottle, such as for example, the conveyor belt of the inspection device that generated the X-ray image data, the tray (if any) on which the bottle was placed during the screen and/or the walls of the bottle holding the liquid.

At step 452, the location information associated with the meniscus derived at step 442 and the geometric information associated with the bottle derived at step 440 are processed in order to derive path length information, wherein the path length information convey an estimated length of a path followed by X-rays through the liquid held in the bottle. Methods for deriving the path length information based on the location information associated with the meniscus derived and the geometric information associated with the bottle will be readily apparent to the person skilled in art in light of the present description and as such will not be described further here.

At step 460, the path length information derived at step 452 and the attenuation information derived at step 450 are processed to assess the threat status associated with the liquid product.

In a specific example of implementation, the path length information derived at step 452 and the attenuation information derived at step 450 are processed to derived characteristics associated with the liquid product (e.g. the density, the effective atomic number ($Z_{eff}$ number) and/or the linear attenuation coefficient). Methods for deriving such characteristics based on path length and attenuation information are well-known in the art and as such will not be described further here. The characteristics associated with the liquid product can then be compared to entries in a database stored in a memory to determine the threat status of the liquid in the bottle. The database provides information mapping characteristics associated with liquids (e.g. density, effective atomic number ($Z_{eff}$ number) and/or linear attenuation coefficient) with addition information such as for example, the nature of the liquid and/or the threat status. It will be appreciated that the above approach for assessing the threat status associated with the liquid product has been presented for the purpose of illustration only and that other approaches making use of path length information and attenuation information to assess the threat status associated with the liquid product without detracting from the spirit of invention.

As will be appreciated in light of the above, the first path of the process, including step 444 and step 446, is associated to an assessment of the threat status of the liquid product using a determined level of fill of the bottle as a factor in the determination of the threat status of the bottle. The second path, including steps 450 452 and 460, is associated to an assessment of the threat status of the liquid product based in part on the length of the path travelled by X-rays through the liquid held by the bottle. Specific examples of implementation may perform the first and second paths either in parallel or in series. Optionally, the steps in the second path may be performed on a conditional basis depending on the results obtained by the steps in the first path.

At step 462, the threat status determined at step 446 based on the level of fill as well as the threat status derived based on the path length data and attenuation information in the X-ray image data derived at step 460 are considered in combination to obtain a level of threat associated with the liquid product.

In a non-limiting example of implementation, if either step 446 or 460 result in the liquid product being classified as a "threat", step 462 will classify the liquid product as a threat.

Once step 462 is completed, the process proceeds to step 408 (shown in FIG. 4*a*) in which information conveying the threat status is released by the processing module 112.

Deriving Location Information Associated with the Meniscus (Step 442)

As described above with reference to FIG. 4B, at step 442, the x-ray image data associated with the liquid product being screened is processed to derive characteristics of a meniscus formed by the liquid in the bottle. The derived characteristics of the meniscus may generally include location information associated with the meniscus and optionally information related to the shape of the meniscus. It will be appreciated that specific derived characteristics of the meniscus may vary from one implementation to the other. For example, in a non-limiting example of implementation, the curvature of the meniscus as would be present where the liquid has a certain viscosity may also be part of the characteristics of the meniscus that could be derived.

In the present section, specific examples of methods for deriving characteristics of the meniscus associated with the meniscus will be presented. It will be readily appreciated by the person skilled in the art that other methods for deriving such characteristics may also be used without detracting from the spirit of the invention.

In a first specific example of implementation, the liquid products are positioned at a known angle (e.g. by means of a tray having an inclined bottom surface) while it is being scanned by the X-ray machine. By setting a bottle filled with liquid in an inclined position, the meniscus will tend to migrate toward one of the extremities of the bottle, in a specific and non-limiting example of implementation, the liquid products are inclined at a 15° angle from the horizontal plane. It can be appreciated that, in other specific examples of implementation, the angle of incline relative to the horizontal plane can be in the range from about 5° to about 30° and preferably in the range from about 10° to about 20°. In a further specific and non-limiting example of implementation, the angle of incline is in the range from about 10° to about 15°. This may be achieved through the use of a tray having an included bottom surface, of the type depicted in FIG. 6 for example. For specific examples of trays allowing positioning liquids products in inclined positions during screening, the reader is invited to refer to PCT International Patent Application serial number PCT/CA2008/002025 filed in the Canadian Receiving Office on Nov. 17, 2008 by Michel Roux et al. and presently pending. The contents of the aforementioned documents are incorporated herein by reference.

As will be observed, based on the level of fill of the bottle, the meniscus formed by the liquid in the bottle will vary in shape and size. For instance, depending on the level of fill of the bottle, the meniscus will end along either the upper wall of the bottle or along the lower wall of the bottle.

FIGS. 7*a* and 7*b* of the drawings show in very simplified form a bottle 700 holding liquid and positioned at an inclined angle of α. As shown, the bottle has an upper wall 704 and a lower wall 710. In the example shown in FIG. 7*b*, the level of fill of the bottle 700 is such that the meniscus appears as an air bubble in the upper end of the bottle and ends along the upper wall 704 of the bottle 700 at point 720 that is along the axis of the bottle. As will be observed, in such circumstances, the lower portion of the meniscus will appear as an upward-facing, parabola in the X-ray image of the bottle. For the purpose of the present description, in such circumstances the meniscus will be referred to as a positive meniscus. As will be observed, for a relatively full commercial bottle, the meniscus will typically be a positive meniscus and will end along the upper wall of the bottle.

In the example shown in FIG. 7*a*, the level of fill of the bottle 700 is such that the meniscus ends along the lower wall 710 of the bottle 700 at point 708 that is along the axis of the bottle. As will be observed, in such circumstances, the upper portion of the meniscus is in contact with the lower wall of the bottle and appears as a downward-facing parabola in the X-ray image of the bottle. For the purpose of the present description, in such circumstances the meniscus will be referred to as a negative meniscus.

In accordance with a specific example of implementation of the invention, the level of fill of a bottle is determined at least in part based on geometric information related to the bottle holding the liquid and on the point (720 or 708 in FIGS. 7*a* and 7*b*) at which the meniscus is in contact with the upper/lower wall of the bottle. In addition, the shape of the meniscus can also be used to validate and/or adapt the geometric information associated with the bottle that was derived in prior steps (step 440 shown in FIG. 4B).

In a non-limiting example of implementation, different approaches may be used for determining the location of the point (708 or 720 in FIGS. 7*a* and 7*b*) at which the meniscus is in contact with the upper/lower wall of the bottle depending on whether we have a positive or negative meniscus. In the section below, examples of different approaches will be described. It will be readily appreciated by the person skilled in the art in light of the present description that other suitable approaches may be contemplated. As such, the approaches presented here are being presented for the purpose of illustration only.

In a specific example of implementation, the detection and characterisation of the meniscus is based at least in part by tracking the changes in the intensity of the gray-shaded areas in an X-ray image as obtained from the X-ray image data generated by the inspection device 102 (shown in FIG. 1).

More specifically, the X-ray image data generated by the inspection device 102 (shown in FIG. 1) provides attenuation information for each {x,y} coordinate in a two-dimensional plane. This attenuation information is typically represented in the form of a greyscale level in an X-ray image. By tracking the change in intensity of the gray scale levels in the X-ray image, a general indication of the surface of the objects depicted in the X-ray image can be obtained.

It can be observed that, for most liquids, the meniscus formed by the liquid in a bottle will be a generally flat surface. Although some minor variations in the surface caused by the viscosity/surface tension of the liquid in the bottle may be present, for most liquids of interest, the assumption that the liquid in the bottle will be a generally flat surface has been found to be a reasonable one. By tracking the change in intensity of the gray scale levels in the X-ray image depicting areas inside the bottle, information pertaining to characteristics of the meniscus' surface as well as the shape of the meniscus can be obtained.

Positive Meniscus

One mechanism that can be used in order to track the change in intensity of the gray scale levels in the X-ray image is the use of surface normals.

Generally speaking, a surface normal, or simply normal, to a flat surface is a vector which is perpendicular to that surface. A normal to a non-flat surface at a point P on the surface is a vector perpendicular to the tangent plane to that surface at P. In the case of a two-dimensional image, such as for example an X-ray image, the intensity information conveyed by the X-ray image data is used to represent the third dimension of the objects being represented.

Another mechanism that can be used in order to track the change in intensity of the gray scale levels in the X-ray image is the use of gradients. In vector calculus, the gradient of a scalar field (e.g. the intensity values represented by the grayscale levels in the X-ray image) is a vector field which points in the direction of the greatest rate of increase of the scalar field, and whose magnitude is the greatest rate of change. In Cartesian coordinates, the gradient may be expressed as follows:

$$\nabla f(x, y) = \left( \frac{\partial f}{\partial dx}, \frac{\partial f}{\partial dy} \right)$$

Where f( ) is the intensity function and "x" and "y" represent the 24) coordinate space in the X-ray image. The gradients can then been used to obtain information on the shape of the meniscus, including identifying the coordinates of the lowest point of the meniscus.

Other mechanisms for tracking such changes may be used and will become readily apparent to the person skilled in the art in light of the present description.

Although surface normals and gradients could be used in situations where the meniscus formed by the liquid in the bottle is either positive or negative, it has been found that the use surface normals and gradients yields more consistent and reliable results in cases where the meniscus is positive.

An exemplary process for using surface normals to detect and characterise a positive meniscus based on X-ray image data will now be described with reference to FIG. 16a.

At step 1600, the X-ray image is processed to locate areas of the image associated to the liquid product. Following this, the computations of the surface normals and subsequent assessments are performed on the identified areas. Advantageously, this allows reducing the number of computations compared to processing to X-ray image as a whole. It will be readily appreciated that step 1600 may be omitted in some implementations.

At step 1602, the X-ray image data generated by the inspection device 102 (or the portion of the X-ray image data identified at step 1600 as corresponding to the liquid product) is filtered to remove noise in the X-ray image. This may be achieved by any suitable mechanism known in the art of image processing. In a non-limiting example of implementation, a low-pass filter designed to remove higher frequency noise in the X-ray image may be used to filter the X-ray image. It will be readily appreciated that step 1602 may be omitted in some implementations.

At step 1604, the X-ray image data is processed to derive an associated pattern of surface normals, where the intensity information of each pixel in the image to designate the third dimension of the X-ray image. Deriving surface normals is well known in the field of computer graphics and as such will not be described in greater detail here.

The surface normals are computed for each (x,y) coordinates in the X-ray image associated with the liquid product under inspection. It will be readily appreciated that, in alternative examples of implementation that omit step 1600, surface normals may be computed for all (x,y) coordinates in the X-ray image.

Figure 10:
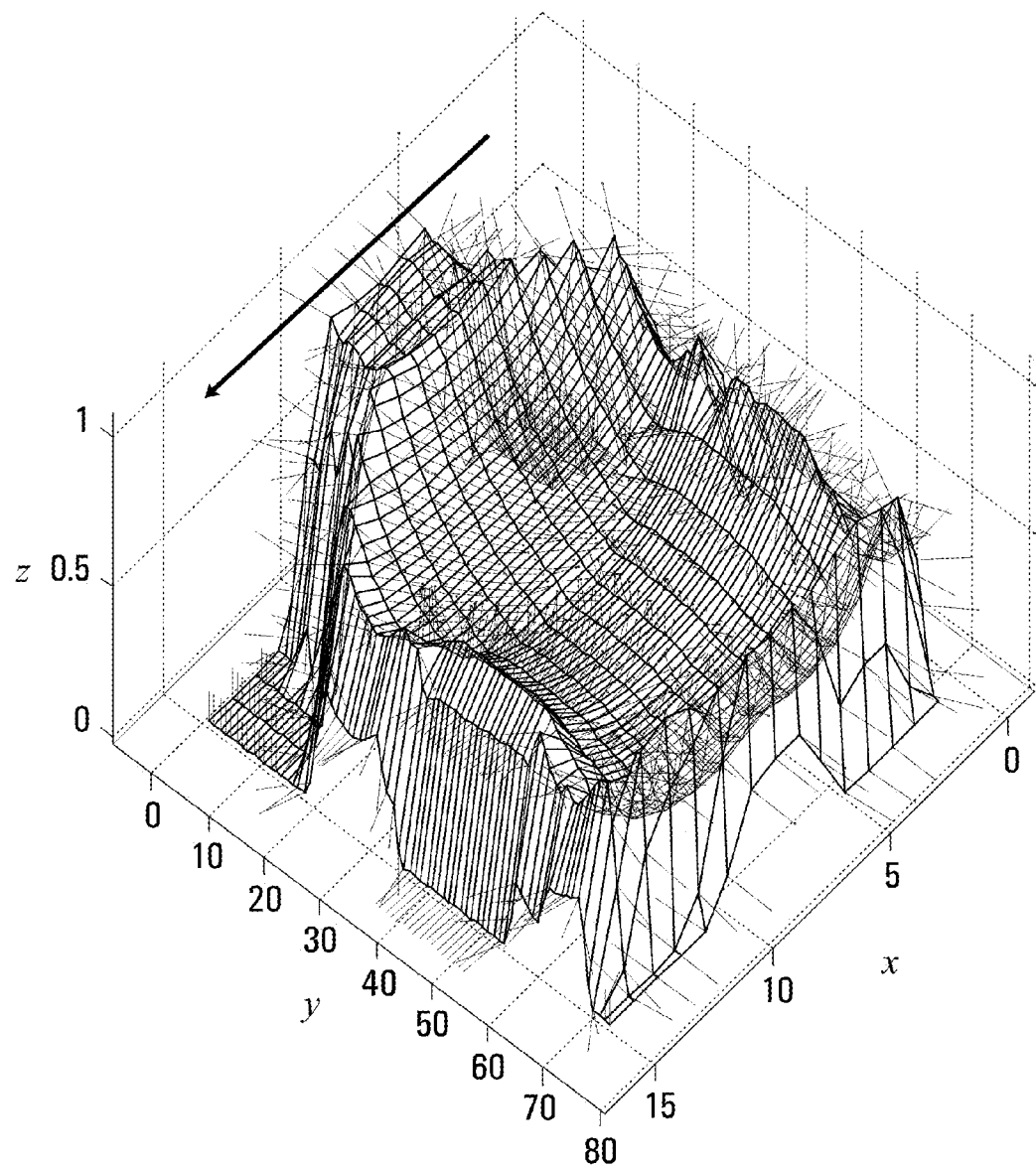
FIG. 10 is a 3-D map of surface normals derived based on an X-ray intensity image of one of the bottles shows in FIG. 9a in accordance with a non-limiting example of implementation of the invention.

FIG. 10 of the drawings depicts in graphical form surface normals derived based on the portion of the X-ray image shown in FIG. 9A corresponding to bottle 900.

Once the surface normals are computed at step 1604, the process proceeds to step 1606.

At step 1606, projections of the surface normals are computed. In a specific example of implementation, projections of the surface normals are obtained in the (x,y) plane, the (y,z) plane and/or the (x,z) plane in order to extract various characteristics pertaining to the shape of the meniscus. Computing projections of surface normals is well-known in the art and as such will not be described in greater detail here.

Figures 11A, 11B, 11C:
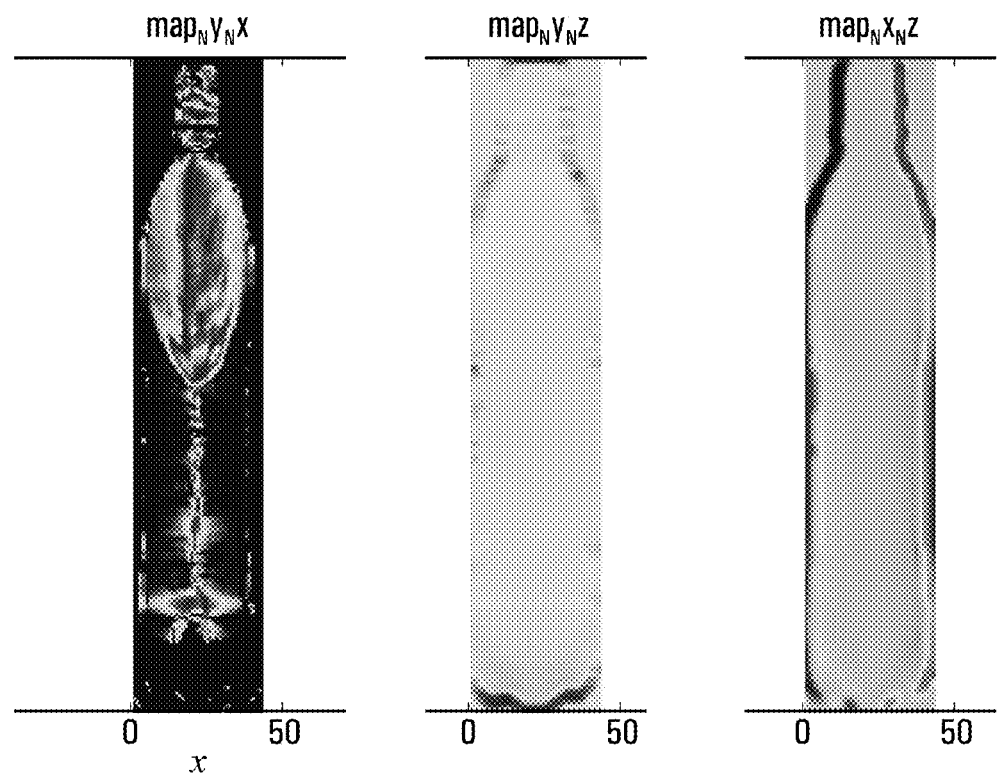
FIGS. 11a 11b and 11c are projections in the x-y, y-z and x-z planes respectively of the 3-D intensity map depicted in FIG. 10 in accordance with a non-limiting example of implementation of the invention.

FIGS. 11a, 11b and 11c of the drawings depict in graphical form projections of the surface normals depicted in FIG. 10 in the (x,y) plane, the (y,z) plane and the (x,z) plane respectively.

The projection of the surface normals on the (x,y) plane (shown in FIG. 11a) provides the main characteristic of the meniscus' surface based on the mapping of the normal of the intensity profile inside the bottles. As can be observed from the projection of the surface normals on the (x,y) plane, the meniscus appears in the form of an upward-facing parabola. The projections on the (x,z) and (y,z) planes (shown in FIGS. 11b and 11c) can be used to filter the main image and to provide information for image segmentation. In addition, the projections on the (x,z) and (y,z) planes can be used to confirm the accuracy of the portion of the X-ray image identified at step 1600 as corresponding to a liquid product.

At step 1608, the location of the point (720 in FIG. 7b) at which the meniscus is in contact with the upper wall of the bottle is determined based on the projection of the surface normals on the (x,y) plane. Amongst others, image segmentation techniques such as threshold calculation, morphology and label analysis may be used in order to isolate the information relative to the meniscus in the projected (x,y) plane. Once the meniscus is isolated, the position corresponding to the lowest point of the parabola can be identified using any suitable image processing method. Such methods are well-known in the art of computer graphics and computer vision and as such will not be described in further detail here.

Once the location of the point (720 in FIG. 7b) at which the meniscus is in contact with the upper wall of the bottle is determined the process proceeds to step 1610.

At step 1610, position information pertaining to the meniscus in the bottle is derived based in part on the location of the point (720 in FIG. 7b) at which the meniscus is in contact with the upper wall of the bottle determine at step 1608 and on the geometric information associated with the bottle derived at step 440 (shown in FIG. 4B). The position information of the meniscus includes, amongst others, information related to the height of the meniscus (in mm) in the bottle. In a non-limiting specific example of implementation, a mathematical 3-D reconstruction of the bottle under inspection will have been generated at step 440 (shown in FIG. 4B) wherein coordinates of the bottle in the X-ray image will have been mapped into a new coordinate space. In such an implementation, the coordinates of the meniscus, including location of the point (720 in FIG. 7*b*) at which the meniscus is in contact with the upper wall of the bottle and the level of the meniscus in the bottle are also mapped into the same coordinate space as the reconstructed bottle using mapping, techniques known in the art of computer graphics.

FIG. 8 provides an example of a coordinate system that may be used for the purpose of positioning the meniscus into a mathematical 3-D reconstruction of the bottle under inspection. The θ and H variables may be estimated in situ using any suitable calibration method.

Figure 12:
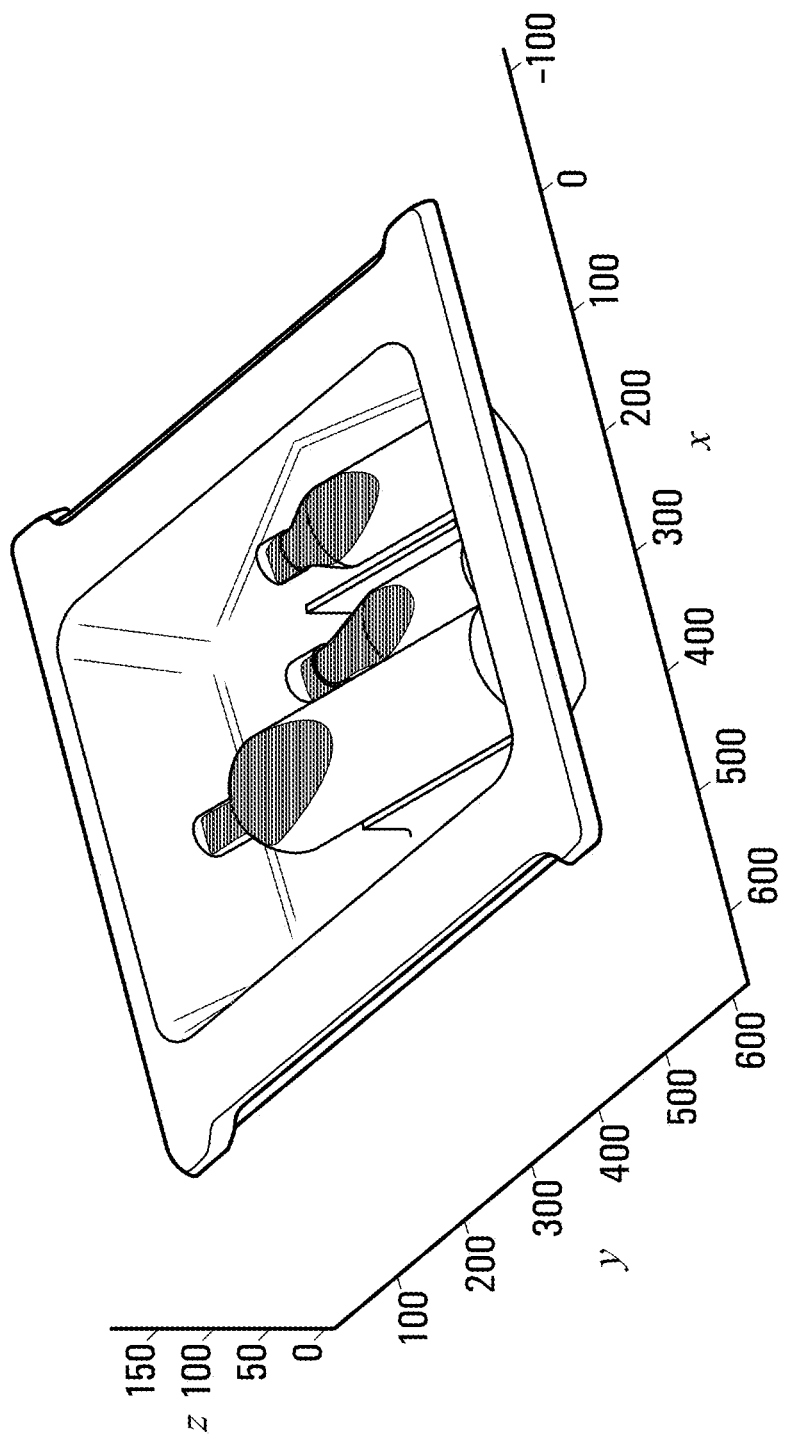
FIG. 12 shows a graphical representation of a scene reconstructed in 3-D from the x-ray image depicted in FIG. 9a in accordance with a specific example of implementation of the invention.

FIG. 12 shows a graphical representation of a scene reconstructed in three-dimensional from the X-ray image depicted in FIG. 9*a* in accordance with a specific example of implementation of the invention. It is to be appreciated that this three-dimensional reconstruction is being presented for the purpose of illustration only.

Negative Meniscus

Another mechanism that can be used in order to track the change in intensity of the gray scale levels in the X-ray image is the use of potentials from which a distance map can be calculated. Although potentials and distance maps can be used in situations where the meniscus formed by the liquid in the bottle is either positive or negative, it has been found that this approach yields more consistent and reliable results in cases where the meniscus is negative.

An exemplary process for using potentials and distance maps to detect and characterise a meniscus based on X-ray image data will now be described with reference to FIG. 16*b*.

Figure 16A:
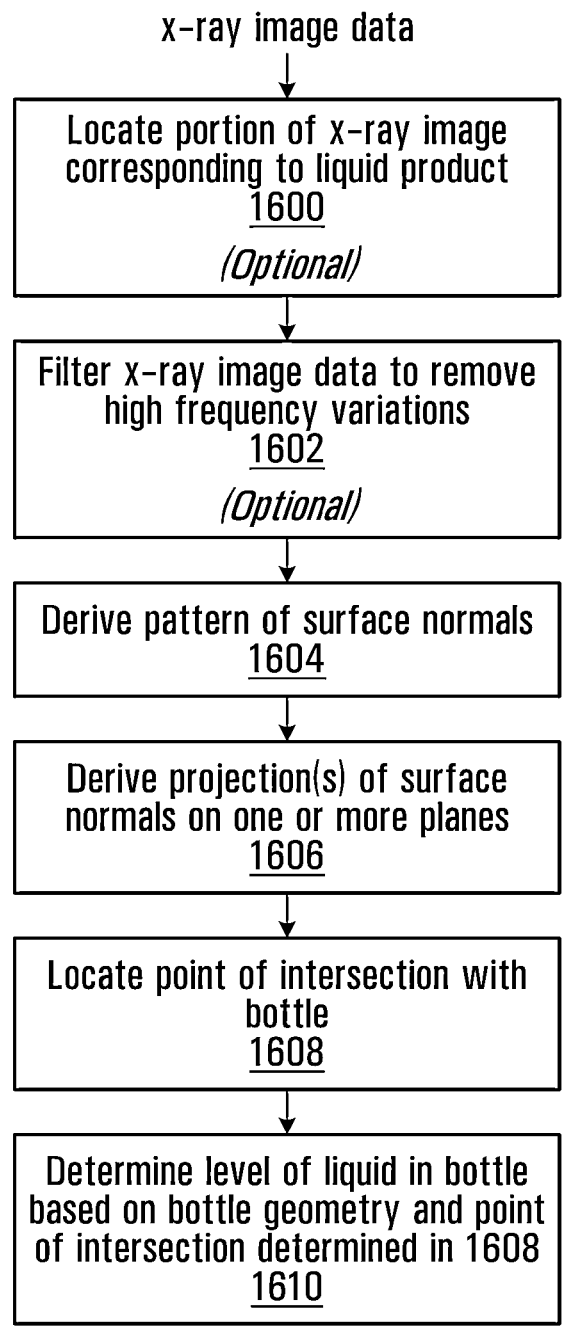
FIG. 16a shows a process for determining location information associated with a meniscus formed by liquid held in a bottle according to a first specific example of implementation of the invention.
Figure 16B:
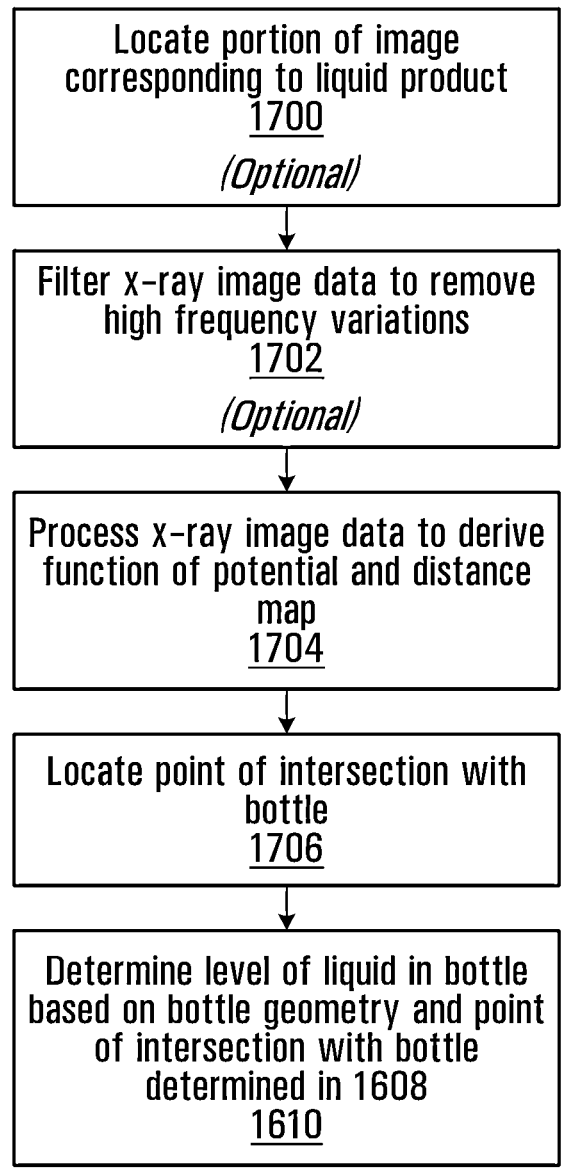
FIG. 16b shows a process for determining location information associated with a meniscus formed by liquid held in a bottle according to a second specific example of implementation of the invention.

At step 1700, which is analogous to step 1600 shown in FIG. 16*a*, the X-ray image is processed to locate areas of the image associated to the liquid product. Following this, the subsequent computations/assessments are performed on the identified areas. Advantageously, this allows reducing the number of computations compared to processing to X-ray image as a whole. It will be readily appreciated that step 1700 may be omitted in some implementations.

At step 1702, which is analogous to step 1702 shown in FIG. 16*a*, the X-ray image data generated by the inspection device 102 (or the portion of the X-ray image data identified at step 1700 as corresponding to the liquid product) is filtered to remove noise in the X-ray image.

At step 1704, the X-ray image data is processed to derive an associated pattern of potentials and a corresponding distance map. More specifically, the intensity information of each pixel in the image is used to designate the potential levels. Deriving potentials is well known in the field of computer graphics and as such will not be described in greater detail here.

Following this, at step 1706 the location of the point (708 in FIG. 7*a*) at which the meniscus is in contact with the lower wall of the bottle is performed based at least in part on the minimization of the distance between two (2) points (a start point and an end point). In a non-limiting example of implementation, the "Fast Marching" method (J. A. Sethian) is used in order to minimize of the distance between two (2) points and derive the location of the point at which the meniscus is in contact with the lower wall of the bottle. The fast marching method is introduced by James Sethian as a numerical method for solving boundary value problems of the form:

$$F(x)|\nabla T(x)|=1.$$

Typically, such a problem describes the evolution of a closed curve as a function of time T with speed F(x) in the normal direction at a point x on the curve. The speed function is specified, and the time at which the contour crosses a point x is obtained by solving the equation. For additional information pertaining to the "Fast Marching" method, the reader is invited to refer to "Level Set Methods and Fast Marching Methods, Evolving Interfaces in Computational Geometry, Fluid Mechanics, Computer Vision, and Materials Science", J. A. Sethian, Cambridge University Press, 1999, Cambridge Monograph on Applied and Computational Mathematics. The content of the aforementioned document are incorporated herein by reference. Another approach is described in "Perception-based 3D Triangle Mesh Segmentation Using Fast Matching Watersheds", by D. L. Page et al., Proc. Intl. Conf. on Computer Vision and Pattern Recognition, Vol. II, pp. 27032, Madison, Wis., June 2008. The content of the aforementioned document are incorporated herein by reference.

In specific example of implementation, in instances where the above described approach yields a solution indicating a positive meniscus, the result is discarded and methods better suited for identifying characteristics for a positive meniscus are used instead, such as a surface normals and/or gradient described above.

Once the location of the point (708 in FIG. 7*a*) at which the meniscus is in contact with the upper wall of the bottle is determined the process proceeds to step 1708.

At step 1708, which is analogous to step 1610 shown in FIG. 16*a*, position information pertaining to the meniscus in the bottle is derived based in part on the location of the point at which the meniscus is in contact with the lower wall of the bottle determine at step 1706 and on the geometric information associated with the bottle derived at step 440 (shown in FIG. 4B). The position information of the meniscus includes, amongst others, information related to the height of the meniscus (in mm) in the bottle.

The person skilled in the art will appreciated that since in typically usage of the system depicted in figures, it will generally not be know a priori whether the meniscus formed by liquid in a bottle is positive or negative, it may be appropriate to perform both a first approach suitable for a negative meniscus and a second approach suitable for a positive meniscus on a same bottle. In a first example of implementation, approaches suitable for positive and negative meniscus are performed sequentially so that if a first one of the approaches yields a results that is unexpected, for example an approach that is more suitable for a positive meniscus yields a results that indicates a negative meniscus or vice versa, then the other approach may be initiated. In a second example of implementation, approaches suitable for positive and negative meniscus are performed in parallel.

Another Example for Deriving Location Information Associated with the Meniscus (Step 442)

Figure 16C:
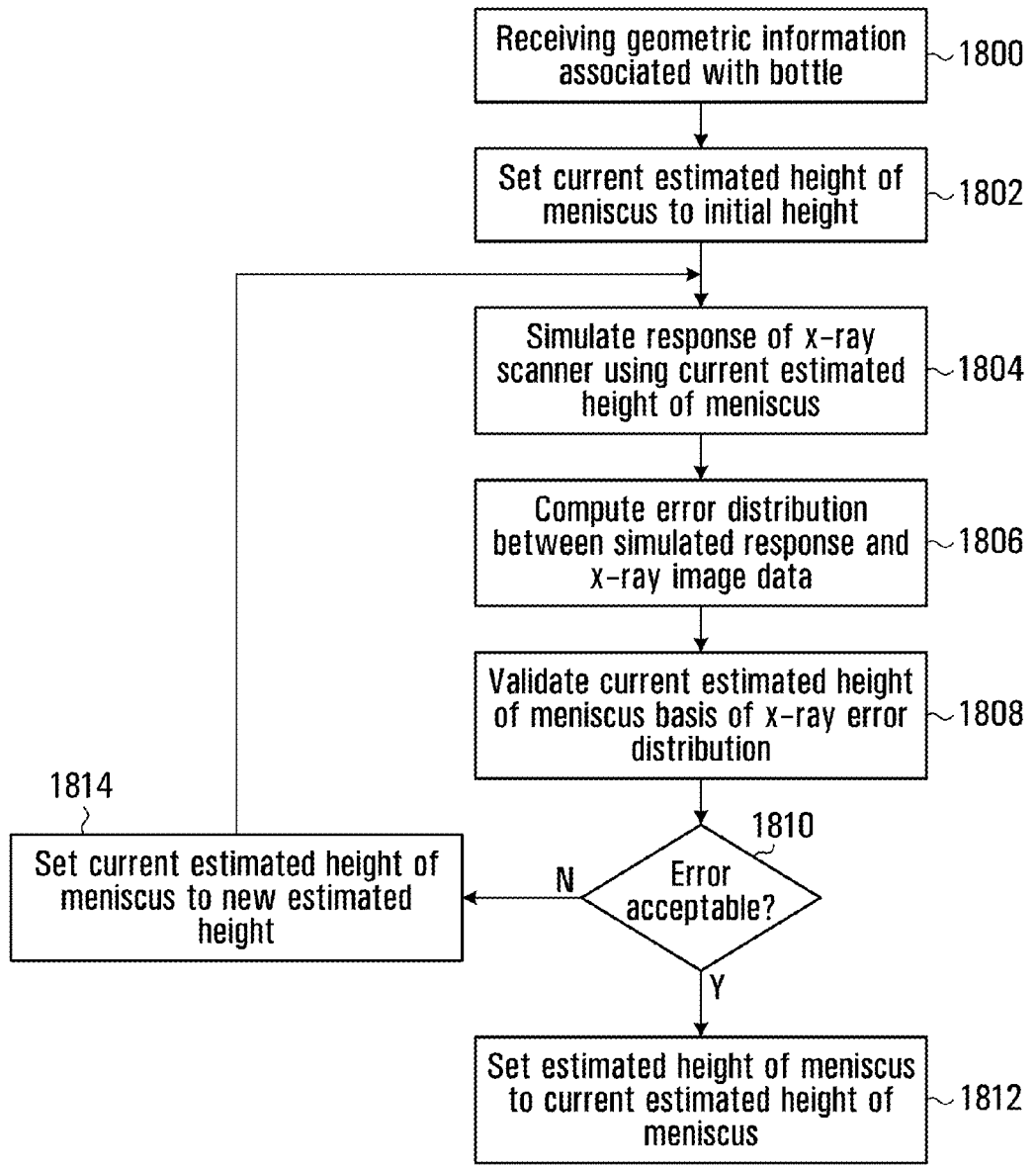
FIG. 16c shows a process for determining location information associated with a meniscus formed by liquid held in a bottle according to a third specific example of implementation of the invention.

Another example for deriving location information associated with the meniscus (step 442) is illustrated in the flowchart shown in FIG. 16*c*.

In this example, the logic works on the basis of an assumption as to the height of the meniscus. The assumption is then subjected to a validation procedure, the results of which are used to modify and or refine the assumption. Optionally, this process may be performed iteratively until a certain condition is met. The condition may be, for example, that a pre-determined number of iterations has been made or that the validation procedure indicates a satisfactory result.

More specifically, the process starts at step 1800 where geometric information associated with the bottle, of the type derived at step 440 shown in FIG. 4B, is received.

Once the geometric information associated with the bottle is available, we proceed to step 1802 where an assumption as to the height of the meniscus is made. In a first specific example of implementation (not shown in the figures), multiple assumptions as to the height of meniscus are made concurrently and processed in parallel in order to identify the most likely height of the meniscus. In this first specific example of implementation the number of assumptions is not limiting and depends on the processing capability of the processing module 112 (shown in FIG. 1) and the desired degree of precision to be attained.

In a second specific example of implementation (shown in FIG. 16*c*), a currently estimated height of the meniscus is set to an initial meniscus height. The specific initial meniscus height selected may vary from one implementation to the other. In a first example, the initial height may be selected based on a default height (distance) of the meniscus from the conveyor belt of the inspection device 102 (shows in FIGS. 1 and 2). Alternatively, the specific initial height is selected based in part on the geometric information associated with the bottle under inspection and received at step 1800 to correspond to a certain height within the bottle, in a non-limiting implementation, the initial height of the meniscus is set to generally correspond to the middle of the bottle.

Following this the process proceeds to step 1804.

At step 1804, the response of the inspection device 102 (shown in FIG. 1) obtained by subjecting the liquid product to X-rays is simulated using a computer implemented simulation engine. The simulation process implemented by the computer implemented simulation engine is a coarse modelling of the operation of the X-ray inspection device 102 and aims deriving the likely X-ray attenuation data that would be obtained when a liquid product having geometric characteristics corresponding to those received at step 1800, filled with a reference liquid, such as water for example, and having a meniscus positioned at the currently estimated height of the meniscus is screened by the X-ray inspection device 102.

The simulation is generally a multi-step process, although it may vary in different implementations. During a first step, a virtual model of the bottle is generated using geometric characteristics received at step 1800 and the currently estimated height of the meniscus according to any suitable method known in the field of computer vision. During a second step, a virtual model of the inspection device 102 is generated and the virtual model of the bottle placed in that model, such as to match the position of the real liquid product in the real inspection device 102. Given those simulated conditions, a model which simulates the interaction of X-rays with the reference liquid is executed to determine what likely attenuation information would be produced. Different types of models can be used without departing from the spirit of the invention.

One example of a model that can be used is one which determines the attenuation to which the X-rays would be subjected, at different locations throughout the liquid product on the basis of theoretical equations that map attenuation with path length, liquid characteristics and X-ray characteristics. Since the X-ray characteristics are known, the liquid characteristics are also known, and the path length can be derived based on the virtual model, an estimate of the attenuation information can be derived.

The result of step 1804 is data conveying estimated X-ray attenuation information.

At step 1806, the attenuation information obtained at step 1804 via the virtual model is compared with the attenuation information in the X-ray image data obtained by scanning the liquid product using the real inspection device 102 (shown in FIGS. 1 and 2). The purpose of the comparison is to determine the error distribution between the two. The attenuation information generated by the model will likely be different from the attenuation information in the X-ray image data since the liquids are likely different. Recall that the model uses a reference liquid, such as water, while the real liquid product is filled most likely with something else. However, if the currently estimated height of the meniscus is generally correct, the attenuation error distribution will be generally uniform. On the other hand, if the currently estimated height of the meniscus is far from the actual height, then the error distribution will not be uniform.

At the validation step 1808, the error distribution obtained at step 1806 is evaluated to determine whether the currently estimated height of the meniscus is likely to be correct. This evaluation may be effected by comparing the error distribution to a reference and/or to an error distribution associated with a different estimated height of the meniscus.

At step 1810 a decision is made as to whether to currently estimated height of the meniscus is satisfactory or whether a new estimated height should be selected. If condition at step 1810 is answered in the negative, the currently estimated height of the meniscus is set to a new estimated height at step 1814. The selection of the new estimated height is made in order to converge to a meniscus height where the variances in the error distribution obtained at step 1806 will be minimized. Steps 1804 1806 1808 and 1810 are then repeated for the new estimated height.

If condition at step 1810 is answered in the positive, the estimated height of the meniscus is set to correspond to the currently estimated height.

Specific Practical Implementation

Figure 13:
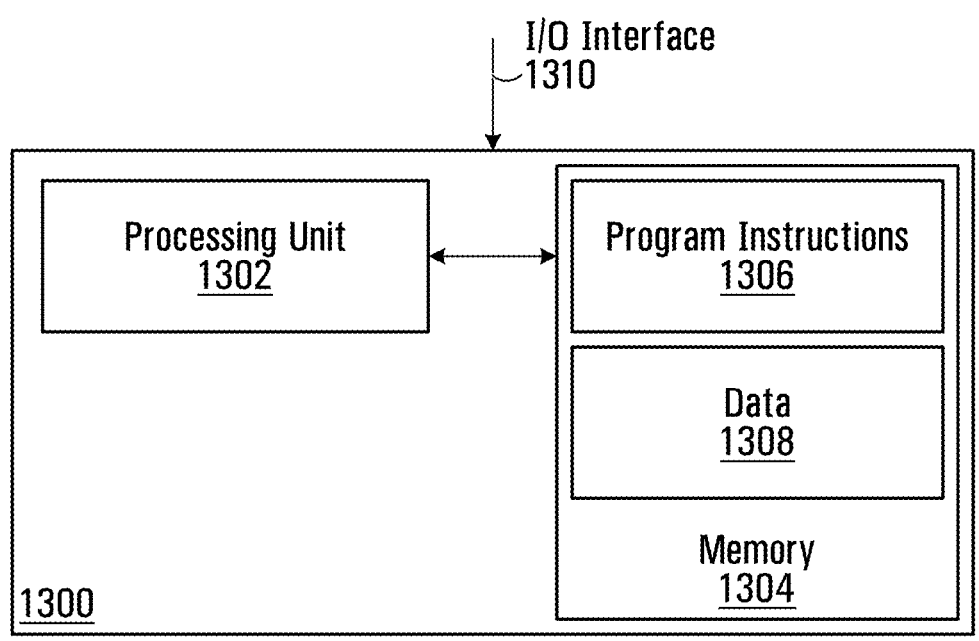
FIG. 13 is a block diagram of a computing apparatus suitable for use in connection with the apparatus illustrated in FIG. 3 in accordance with a specific example of implementation of the invention.

Certain portions of the processing module 112 (shown in FIGS. 1 and 3) may be implemented on a general purpose digital computer 1300, of the type depicted in FIG. 13, including a processing unit 1302 and a memory 1304 connected by a communication bus. The memory 1304 stores data 1308 and program instructions 1306. The processing unit 1302 is adapted to process the data 1308 and the program instructions 1306 in order to implement the functions described in the specification and depicted in the drawings. The digital computer 1300 may also comprise an I/O interface 1310 for receiving or sending data elements to external devices, such as the for example the inspection device 102 and the display device 150 (both shown in FIG. 1).

Alternatively, the above-described processing module 112 can be implemented on a dedicated hardware platform where electrical/optical components implement the functions described in the specification and depicted in the drawings. Specific implementations may be realized using ICs, ASICs, DSPs, FPGA, an optical correlator, digital correlator or other suitable hardware platform.

Figure 14:
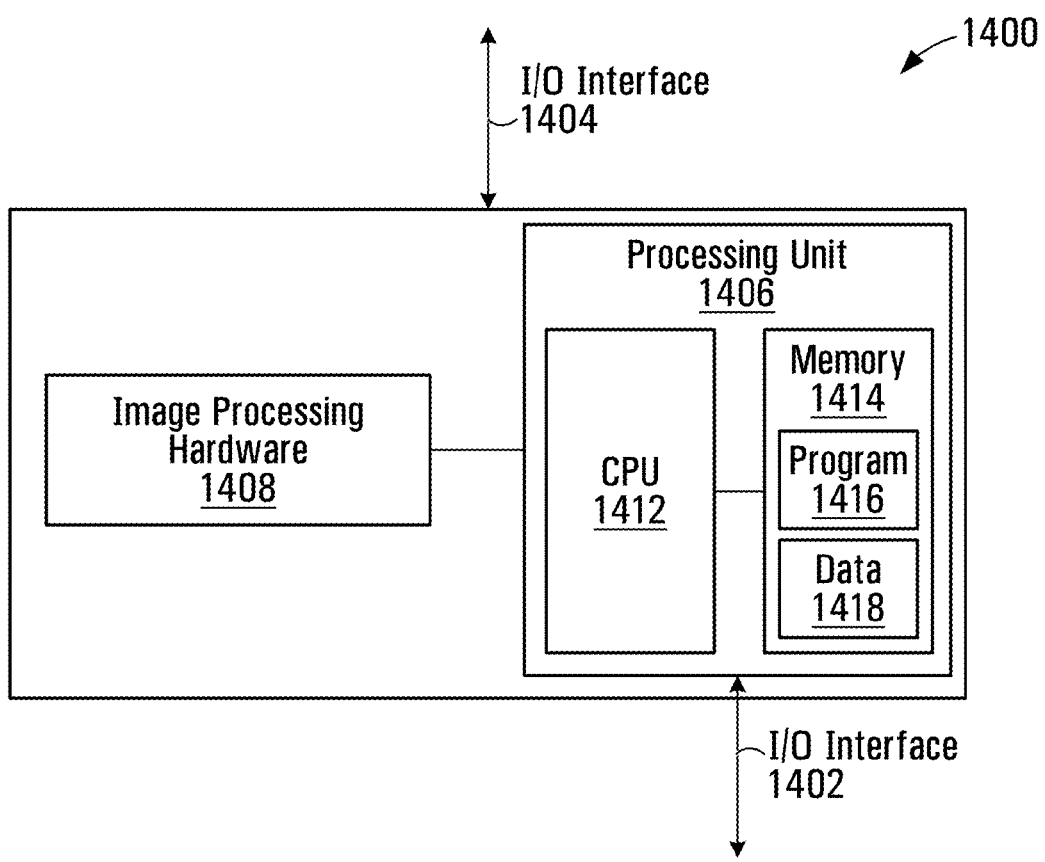
FIG. 14 is a block diagram of a computing apparatus suitable for use in connection with the apparatus illustrated in FIG. 3 in accordance with an alternative specific example of implementation of the invention.

Other alternative implementations of the processing module 112 can be implemented as a combination of dedicated hardware and software, of the type depicted in FIG. 14 and generally designated by reference numeral 1400. Such an implementation comprises a dedicated image processing hardware module 1408 and a general purpose computing unit 1406 including a CPU 1412 and a memory 1414 connected by a communication bus. The memory 1414 stores data 1418 and program instructions 1416. The CPU 1412 is adapted to process the data 1418 and the program instructions 1416 in order to implement the functions described in the specification and depicted in the drawings. As depicted, this specific implementation also comprise one or more I/O interfaces 1404 1402 for receiving or sending data elements to external devices such as, for example, inspection and display devices of the type depicted in FIG. 1.

It will also be appreciated that the screening system 100 that is depicted in FIG. 1 may also be of a distributed nature where the X-ray images are obtained by an inspection device in one location (or more than one location) and transmitted over a network to another entity implementing the functionality of the processing module 112 described above. Another unit may then transmit a signal for causing one or more display devices to display information to the user, such as the X-ray image of the objects being scanned. The display device may be located in the same location where the X-ray images of objects were obtained or in an alternate location. In a non-limiting implementation, the display device may be part of a centralized screening facility.

Figure 15:
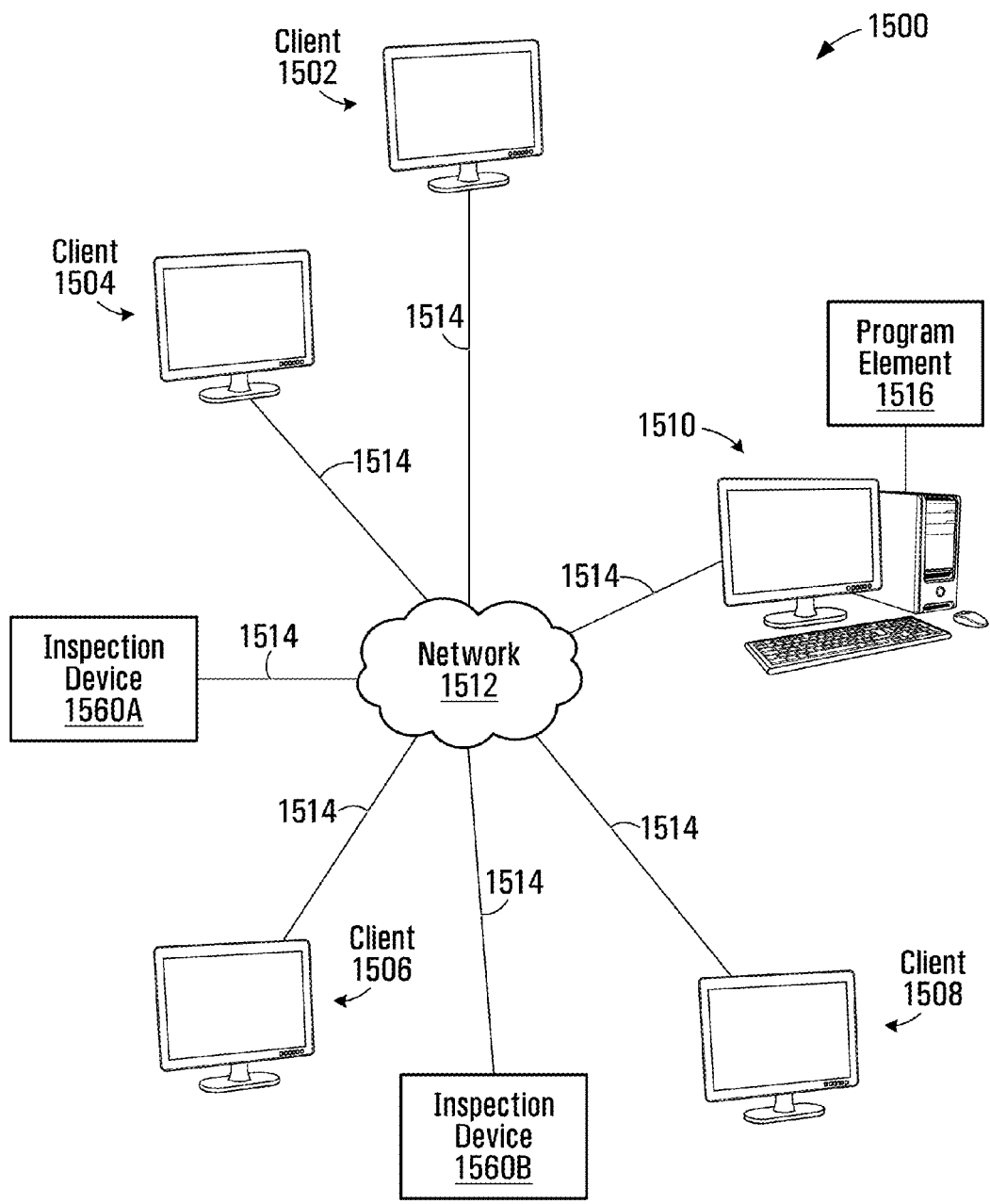
FIG. 15 shows a functional block diagram of a client-server system suitable for implementing for assessing the threat status of a liquid product at a security checkpoint in accordance with an alternative specific example of implementation of the present invention.

FIG. 15 illustrates a network-based client-server system 1500 for screening objects in accordance with a specific example of implementation of the invention. The client-server system 1500 includes a plurality of client systems 1502, 1504, 1506 and 1508 and inspections devices 1560A 1560B connected to a server system 1510 through network 1512. The communication links 1514 between the client systems 1502, 1504, 1506, 1508, the inspections devices 1560A 1560B and the server system 1510 can be metallic conductors, optical fibers or wireless, without departing from the spirit of the invention. The network 1512 may be any suitable network including but not limited to a global public network such as the Internet, a private network and a wireless network. The server 1510 may be adapted to process information received from the inspections devices 1560A 1560B and issue signals conveying screening results to the client systems 1502, 1504, 1506, 1508 using suitable methods known in the computer related arts.

The server system 1510 includes a program element 1516 for execution by a CPU (not shown). Program element 1516 includes functionality to implement the functionality of processing module 112 (shown in FIGS. 1 and 3) described above. Program element 1516 also includes the necessary networking functionality to allow the server system 1510 to communicate with the client systems 1502, 1504, 1506, 1508 and inspections devices 1560A 1560B over network 1512. In a specific implementation, the client systems 1502, 1504, 1506 and 1508 include display devices responsive to signals received from the server system 1510 for displaying screening results derived by the server system 1510.

Although the above embodiments have been described with reference to an inspection device 102 (shows in FIGS. 1 and 2) embodied single view X-ray imaging apparatus, it is to be appreciated that embodiments of the invention may be used in connection with any suitable type of inspection device including multi-view X-ray imaging apparatus.

As such, in an alternative example of implementation, the inspection device 102 is embodied as a multi-view X-ray machine. The multi-view X-ray machine generates X-ray image data associated with the liquid product conveying a first X-ray image of the liquid product taken by subjecting the liquid product to X-rays in a first orientation and a second X-ray image of the liquid product taken by subjecting the liquid product to X-rays in a second orientation. The first and second orientations are different from one another and will frequently be orthogonal to one another, although that may depending on the X-ray machine being used. In such an alternative implementation, the X-ray image data corresponding to the first X-ray image of the liquid product may be processed to derive information associated with the location of the meniscus, information conveying an estimated level of fill of the bottle and/or information pertaining to the threat status of the liquid product according to the methods described above. The X-ray image data corresponding to the second X-ray image of the liquid product is then processed to validate and/or adjust the information derived based on the X-ray image of the liquid product. For example, the X-ray image data corresponding to the second X-ray image and the location information associated with the meniscus obtained based on the X-ray image data corresponding to the first X-ray image may be processed to derive adjusted location information associated with the meniscus. In a non-limiting example of implementation, the adjusted location information associated with the meniscus may be set to the mean between the location information associated with the meniscus derived based on the first X-ray image and that derived based on the second X-ray image. IN another example, the X-ray image data corresponding to the second X-ray image and the level of fill of the bottle obtained based on the X-ray image data corresponding to the first X-ray image may be processed to derive an adjusted level of fill. The threat status of the liquid product may be derived based on the adjusted level of fill of the bottle and/or adjusted location information associated with the meniscus for example.

An advantage of using a multi-view X-ray imaging apparatus, compared to the use of a single view X-ray imaging apparatus, is that the additional view provide three-dimensional information that is unavailable from single two-dimensional view.

It will also be appreciated that the multi-view X-ray machine may generate X-ray image data conveying X-ray images of the liquid taken by subjecting the liquid product to X-rays more that two orientations there by generated three of more X-ray images.

It will therefore be appreciated that other various modifications will become apparent to those skilled in the art and are within the scope of this invention, which is defined more particularly by the attached claims.

The invention claimed is:

1. A method for assessing a threat status of a liquid product at a security checkpoint, the liquid product being comprised of a bottle holding a liquid, wherein the bottle is at least partially filled with liquid, the method comprising:
   a) receiving image data associated with the liquid product conveying an image of the liquid product, the image data being derived by performing a scan of the liquid product at the security checkpoint using an imaging apparatus that uses penetrating radiation;
   b) processing the image data to derive information conveying a level of fill of the bottle, wherein processing image data includes:
      i) processing the image data to derive geometric information associated with the bottle; and
      ii) deriving the level of fill of the bottle at least in part based on the geometric information associated with the bottle;
   c) determining the threat status of the liquid product at least in part based on the level of fill of the bottle;
   d) releasing information conveying the determined threat status of the liquid product.

2. A method as defined in claim 1, wherein determining the threat status of liquid product comprises classifying the liquid product as a threat when the level of fill of the bottle is below a threshold level of fill.

3. A method as defined in claim 1, wherein processing the image data to derive information conveying the level of fill of the bottle comprises locating a meniscus formed by the liquid in the bottle.

4. A method as defined in claim 1, wherein the image data conveys a first image of the liquid product taken by subjecting the liquid product to rays of penetrating radiation in a first orientation and a second image of the liquid product taken by subjecting the liquid product to rays of penetrating radiation in a second orientation, wherein the information conveying the level of fill of the bottle conveys an adjusted level of fill of the bottle and wherein deriving said adjusted level of fill of the bottle comprises:
   a) processing the image data corresponding to the first image of the liquid product to derive information conveying an estimated level of fill of the bottle holding the liquid at least in part based on the image data corresponding to the first image of the liquid product;
   b) processing the image data corresponding to the second image of the liquid product and the estimated level of fill of the bottle obtained based on the image data corresponding to the first image to derive said adjusted level of fill of the bottle.

5. A method as defined in claim 1, wherein the bottle has a cross-sectional shape selected from the set consisting of a generally circular shape, a generally elliptical shape, generally rectangular shape and a generally square shape.

6. A computer program product stored on one or more non-transitory tangible computer readable storage media for assessing a threat status of a liquid product at a security checkpoint, the liquid product being comprised of a bottle holding a liquid, wherein the bottle is at least partially filled with liquid, the program product comprising instructions that, when executed, cause a programmable system including at least one programmable processor to perform operations, the operations comprising:
   i) receiving image data associated with the liquid product conveying an image of the liquid product, the image data being derived by performing an scan of the liquid product at the security checkpoint using an imaging apparatus that uses penetrating radiation;
   ii) processing the image data to derive information conveying a level of fill of the bottle, wherein processing the image data includes: (1) processing the image data to derive geometric information associated with the bottle; and (2) deriving the level of fill of the bottle at least in part based on the geometric information associated with the bottle;
   iii) determining the threat status of the liquid product at least in part based on the level of fill of the bottle;
   iv) releasing information conveying the determined threat status of the liquid product.

7. An apparatus for assessing a threat status of a liquid product at a security checkpoint, the liquid product being comprised of a bottle holding a liquid, wherein the bottle is at least partially filled with liquid, said apparatus comprising an input, a processing unit and an output, said apparatus comprising:
   a) an input for receiving image data associated with the liquid product conveying an image of the liquid product, the image data being derived by performing an scan of the liquid product at the security checkpoint using an imaging apparatus that uses penetrating radiation;
   b) a processing element in communication with said input, said processing element being programmed to:
   i) process the image data to derive geometric information associated with the bottle; and
   ii) process the image data to derive information conveying a level of fill of the bottle, wherein the information conveying the level of fill of the bottle is derived at least in part based on the derived geometric information associated with the bottle; and
   iii) determine the threat status of the liquid product at least in part based on the level of fill of the bottle;
   c) an output for releasing information conveying the determined threat status of the liquid product.

8. A method as defined in claim 1, wherein processing the image data to derive information conveying the level of fill of the bottle includes simulating responses to penetrating radiation of a virtual model of the bottle for different meniscus locations.

9. A method as defined in claim 8, wherein processing the image data to derive information conveying the level of fill of the bottle includes selecting a candidate meniscus location from the different meniscus locations, the selection being performed at least in part based on the simulated responses of the virtual model of the bottle and on the image data.

10. A method as defined in claim 9, wherein the selection is performed at least in part based on a comparison between the simulated responses of the virtual model of the bottle and the image data.

11. A method as defined in claim 8, wherein simulating responses of the virtual model of the bottle to penetrating radiation includes:
   a) simulating a first response of the virtual model of the bottle to penetrating radiation for a first candidate meniscus location;
   b) simulating a second response of the virtual model of the bottle to penetrating radiation for a second candidate meniscus location, the second meniscus location being selected at least in part based on the first candidate meniscus location and a comparison between the image data and the first simulated response.

12. A method as defined in claim 1, wherein processing the image data to derive information conveying the level of fill of the bottle includes:
   i) processing the derived geometric information to derive a virtual model of the bottle;
   ii) simulating responses of the derived virtual model of the bottle to penetrating radiation for different meniscus locations.

13. A computer program product as defined in claim 6, wherein determining the threat status of the liquid product comprises classifying the liquid product as a threat when the level of fill of the bottle is below a threshold level of fill.

14. A computer program product as defined in claim 6, wherein processing the image data to derive information conveying the level of fill of the bottle comprises locating a meniscus formed by the liquid in the bottle.

15. A computer program product as defined in claim 6, wherein the image data conveys a first image of the liquid product taken by subjecting the liquid product to rays of penetrating radiation in a first orientation and a second image of the liquid product taken by subjecting the liquid product to rays of penetrating radiation in a second orientation, wherein the derived information conveying the level of fill of the bottle conveys an adjusted level of fill of the bottle and wherein deriving said adjusted level of fill of the bottle comprises:
   a) processing the image data corresponding to the first image of the liquid product to derive information conveying an estimated level of fill of the bottle holding the liquid at least in part based on the image data corresponding to the first image of the liquid product;
   b) processing the image data corresponding to the second image of the liquid product and the estimated level of fill of the bottle obtained based on the image data corresponding to the first image to derive said adjusted level of fill of the bottle.

16. A computer program product as defined in claim 6, wherein the bottle has a cross-sectional shape selected from the set consisting of a generally circular shape, a generally elliptical shape, generally rectangular shape and a generally square shape.

17. A computer program product as defined in claim 6, wherein processing the image data to derive information conveying the level of fill of the bottle includes simulating responses of a virtual model of the bottle to penetrating radiation for different meniscus locations.

18. A computer program product as defined in claim 17, wherein processing the image data to derive information conveying the level of fill of the bottle includes selecting a candidate meniscus location from the different meniscus locations, the selection being performed at least in part based on a comparison between the simulated responses of the virtual model of the bottle and the image data.

19. A computer program product as defined in claim 17, wherein simulating responses of the virtual model of the bottle to penetrating radiation includes:
 a) simulating a first response of the virtual model of the bottle to penetrating radiation for a first candidate meniscus location;
 b) simulating a second response of the virtual model of the bottle to penetrating radiation for a second candidate meniscus location, the second meniscus location being selected at least in part based on the first candidate meniscus location and a comparison between the image data and the first simulated response.

20. A computer program product as defined in claim 6, wherein processing the image data to derive information conveying the level of fill of the bottle includes:
 i) processing the derived geometric information to derive a virtual model of the bottle;
 ii) simulating responses of the derived virtual model of the bottle to penetrating radiation for different meniscus locations.

21. An apparatus as defined in claim 7, wherein said processing element is programmed to determine the threat status of the liquid product at least in part based on the level of fill of the bottle at least in part by classifying the liquid product as a threat when the level of fill of the bottle is below a threshold level of fill.

22. An apparatus as defined in claim 7, wherein said processing element is programmed to process the image data to derive information conveying the level of fill of the bottle at least in part by processing the image data to locate a meniscus formed by the liquid in the bottle.

23. An apparatus as defined in claim 7, wherein the image data conveys a first image of the liquid product taken by subjecting the liquid product to rays of penetrating radiation in a first orientation and a second image of the liquid product taken by subjecting the liquid product to rays of penetrating radiation in a second orientation, wherein the information conveying the level of fill of the bottle conveys an adjusted level of fill of the bottle and wherein said adjusted level of fill of the bottle is derived by said processing element being further programmed to:
 a) process the image data corresponding to the first image of the liquid product to derive information conveying an estimated level of fill of the bottle holding the liquid at least in part based on the image data corresponding to the first image of the liquid product;
 b) process the image data corresponding to the second image of the liquid product and the estimated level of fill of the bottle obtained based on the image data corresponding to the first image to derive said adjusted level of fill of the bottle.

24. An apparatus as defined in claim 7, wherein the bottle has a cross-sectional shape selected from the set consisting of a generally circular shape, a generally elliptical shape, generally rectangular shape and a generally square shape.

25. An apparatus as defined in claim 7, wherein processing the image data to derive information conveying the level of fill of the bottle includes simulating responses of a virtual model of the bottle to penetrating radiation for different meniscus locations.

26. An apparatus as defined in claim 25, wherein processing the image data to derive information conveying the level of fill of the bottle includes selecting a candidate meniscus location from the different meniscus locations, the selection being performed at least in part based on the simulated responses of the virtual model of the bottle and on the image data.

27. An apparatus as defined in claim 26, wherein the selection is performed at least in part based on a comparison between the simulated responses of the virtual model of the bottle and the image data.

28. An apparatus as defined in claim 25, wherein simulating responses of the virtual model of the bottle to penetrating radiation includes:
 a. simulating a first response of the virtual model of the bottle to penetrating radiation for a first candidate meniscus location;
 b. simulating a second response of the virtual model of the bottle to penetrating radiation for a second candidate meniscus location, the second meniscus location being selected at least in part based on the first candidate meniscus location and a comparison between the image data and the first simulated response.

29. An apparatus as defined in claim 7, wherein processing the image data to derive information conveying the level of fill of the bottle includes:
 iii) processing the derived geometric information to derive a virtual model of the bottle;
 iv) simulating responses of the derived virtual model of the bottle to penetrating radiation for different meniscus locations.

* * * * *